United States Patent
Tovey et al.

(10) Patent No.: US 10,628,874 B2
(45) Date of Patent: Apr. 21, 2020

(54) SYSTEMS AND METHODS FOR AUTOMATICALLY ORDERING A PRODUCT ITEM VIA A WEARABLE TECHNOLOGY

(71) Applicant: Walmart Apollo, LLC, Bentonville, AR (US)

(72) Inventors: David G. Tovey, Rogers, AR (US); Bruce W. Wilkinson, Rogers, AR (US); Kurt W. R. Bessel, Mexico, NY (US)

(73) Assignee: Walmart Apollo, LLC, Bentonville, AR (US)

( * ) Notice: Subject to any disclaimer, the term of this patent is extended or adjusted under 35 U.S.C. 154(b) by 0 days.

(21) Appl. No.: 16/369,363

(22) Filed: Mar. 29, 2019

(65) Prior Publication Data

US 2019/0325502 A1 Oct. 24, 2019

Related U.S. Application Data

(60) Provisional application No. 62/659,934, filed on Apr. 19, 2018.

(51) Int. Cl.
*G06Q 30/06* (2012.01)
*H04B 1/3827* (2015.01)
(Continued)

(52) U.S. Cl.
CPC ......... *G06Q 30/0635* (2013.01); *G16H 20/10* (2018.01); *G16H 40/20* (2018.01); *H04B 1/385* (2013.01); *H04W 4/029* (2018.02)

(58) Field of Classification Search
CPC .............. G06Q 30/06; G06Q 30/0641; G06Q 30/0601; H04M 3/523; G06F 19/00;
(Continued)

(56) References Cited

U.S. PATENT DOCUMENTS 8,945,017 B2  2/2015 Venkatraman
2012/0041767 A1  2/2012 Hoffman
(Continued)

OTHER PUBLICATIONS

PCT; App. No. PCT/US2019/025952; International Search Report and Written Opinion dated Jun. 28, 2019.
Anderson, Janna et al.; "The Internet of Things Will Thrive by 2025"; https://www.pewinternet.org/2014/05/14/internet-of-things; May 14, 2014; pp. 1-14.
(Continued)

*Primary Examiner* — Joseph D Burgess
(74) *Attorney, Agent, or Firm* — Fitch, Even, Tabin & Flannery LLP

(57) ABSTRACT

In some embodiments, apparatuses and methods are provided herein useful to automatically order. In some embodiments, there is provided a system for automatically ordering a product item including at least one first sensor, at least one smart-device interface, a remote database, and at least one control circuit configured to: determine whether a signaling data is received; communicatively couple with the at least one smart device; prompt a user to select; determine whether a previously stored data has been stored; delete the previously stored data; copy a plurality of urgency threshold values; access the first sensed data; access the second sensed data; determine a product item; determine whether the at least one of: the first sensed data and the second sensed data has reached an urgency threshold value; and automatically initiate ordering and delivery of the product item when the urgency threshold value has been reached.

22 Claims, 9 Drawing Sheets

(51) Int. Cl.
*G16H 20/10* (2018.01)
*G16H 40/20* (2018.01)
*H04W 4/029* (2018.01)

(58) Field of Classification Search
CPC ............ G06F 1/16; G06F 17/30; G06F 1/163; G06K 7/10; A61B 5/00
See application file for complete search history.

(56) References Cited

U.S. PATENT DOCUMENTS

| | | | |
|---|---|---|---|
| 2014/0052567 A1 | 2/2014 | Bhardwaj | |
| 2014/0236652 A1 | 8/2014 | Argue | |
| 2014/0349256 A1* | 11/2014 | Connor | G09B 19/0092 434/127 |
| 2015/0045631 A1 | 2/2015 | Ademola | |
| 2016/0125677 A1* | 5/2016 | Williams | G07C 9/00111 340/5.81 |
| 2017/0031449 A1 | 2/2017 | Karsten | |
| 2017/0098268 A1 | 4/2017 | Karvela | |
| 2017/0109806 A1 | 4/2017 | Adoni | |
| 2017/0148348 A1 | 5/2017 | Hardee | |
| 2017/0323057 A1* | 11/2017 | Karvela | G06K 7/10891 |

OTHER PUBLICATIONS

Biostrap; "How It Works"; https://biostrap.com/#how-it-works; Oct. 3, 2017; pp. 1-9.
Coolthings; "This Wearable Inflatable Auto-Deploys When It Detects Imminent Drowning Danger"; https://www.coolthings.com/ploota-sensor-controlled-water-safety-device; May 11, 2017; pp. 1-10.
IMT Staff; "How Wearable Technologies Can Transform Field Service and Maintenance"; https://www.engineering.com/Blogs/tabid/3207/ArticleID/8417/How-Wearable-Technologies-Can-Transform-Field-Service-and-Maintenance.aspx; Sep. 5, 2014; pp. 1-3.
Kenney, Briley; "The Best GPS Trackers and Senior Wearables: Updated for 2017"; https://smartwatches.org/learn/best-senior-wearables-gps-trackers; Jul. 31, 2015; pp. 1-18.
Leung, Stuart; "How Wearable Technology Can (And Will) Change Your Business"; https://www.forbes.com/sites/salesforce/2014/09/07/wearable-tech-business/#160e75fcbae0; Jul. 1, 2014; pp. 1-5.
Mouser Electronics; "The Internet of Things"; https://www.mouser.com/applications/article-iot-wearable-devices; Available at least as early as Oct. 25, 2017; pp. 1-3.
Zhou, Louise; "Ubicomp: Fresh Band—Louise Zhou"; http://www.louise-zhou.com/ubicomp-fresh-band; Available at least as early as Sep. 27, 2017; pp. 1-8.

* cited by examiner

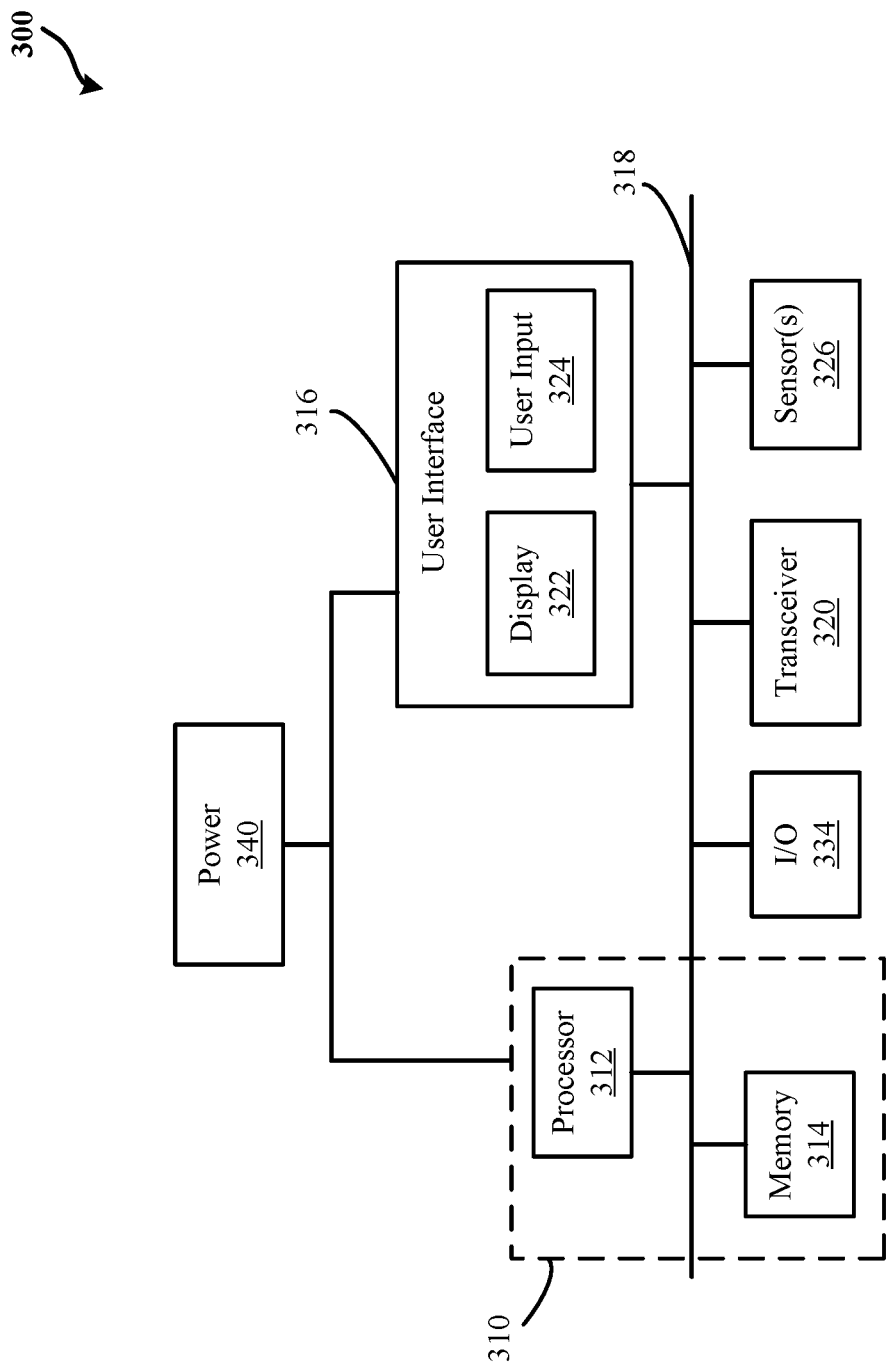

SYSTEMS AND METHODS FOR AUTOMATICALLY ORDERING A PRODUCT ITEM VIA A WEARABLE TECHNOLOGY

CROSS-REFERENCE TO RELATED APPLICATION

This application claims the benefit of U.S. Provisional Application No. 62/659,934 filed Apr. 19, 2018, which is incorporated herein by reference in its entirety.

TECHNICAL FIELD

This invention relates generally to automatically ordering a product item.

BACKGROUND

Generally, when a customer buys an item, the customer makes a decision to buy and consciously and physically pay for the item by giving cash or swiping a credit card at a retail store or by entering a credit card number when shopping online.

BRIEF DESCRIPTION OF THE DRAWINGS

Disclosed herein are embodiments of systems, apparatuses and methods pertaining to automatically ordering a product item. This description includes drawings, wherein:

FIG. 3 illustrates an exemplary system for use in implementing methods, techniques, devices, apparatuses, systems, servers, sources and monitoring item distribution, in accordance with some embodiments;

Figure 1:
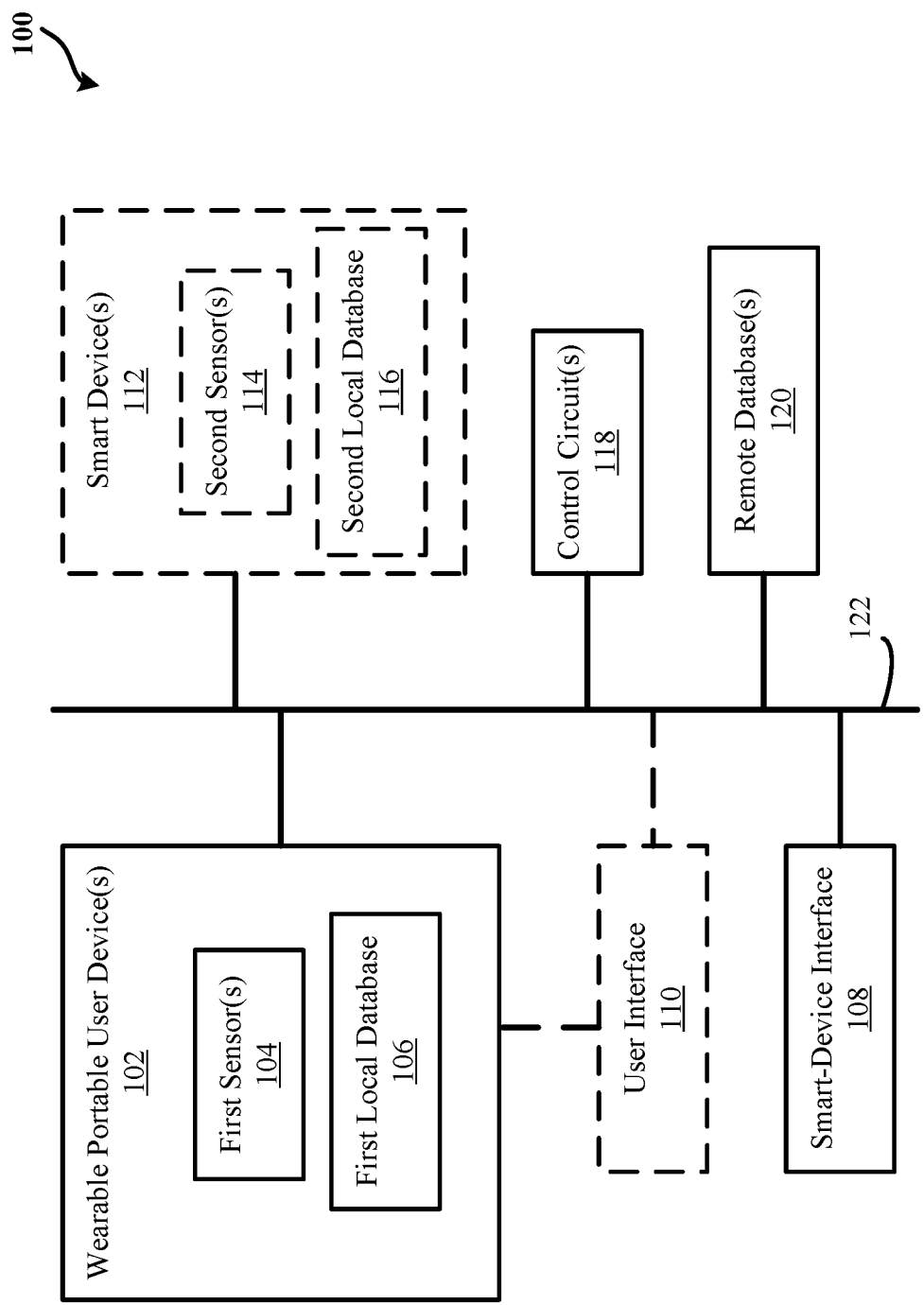
FIG. 1 illustrates a simplified block diagram of an exemplary system for automatically ordering a product item in accordance with some embodiments.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to various embodiments, systems, apparatuses and methods are provided herein useful for automatically ordering a product item. In some embodiments, a system for automatically ordering a product item associated with sensed data from at least one sensor of a wearable portable user device includes at least one first sensor. By one approach, the at least one first sensor may provide a first sensed data of a user of a wearable portable user device. In one configuration, the system may include at least one smart-device interface. By one approach, the at least one smart-device interface may receive at least one of: signaling data, default sensing exception data, and second sensed data associated with at least one smart device. In another configuration, the system may include at least one control circuit coupled to the at least one sensor and the at least one smart-device interface. In one implementation, the at least one control circuit may determine whether the signaling data is received from the at least one smart-device interface at a first time. In another implementation, the at least one control circuit may communicatively couple with the at least one smart device via the at least one smart-device interface in response to the determination that the signaling data is received. Alternatively or in addition to, the at least one control circuit may, in response to communicatively coupling with the at least one smart device, prompt the user to select whether a first local database of the wearable portable user device or a second local database of the at least one smart device stores the first sensed data from the at least one first sensor and the second sensed data associated with the at least one smart device. Alternatively or in addition to, the at least one control circuit may, in response to the user selecting the second local database of the at least one smart device, determine whether a previously stored data has been stored in the second local database for a time period at least equal to a threshold value. Alternatively or in addition to, the at least one control circuit may delete the previously stored data from the second local database in response to the determination that the previously stored data has been stored in the second local database for the time period at least equal to the threshold value. Alternatively or in addition to, the at least one control circuit may copy a plurality of urgency threshold values from a remote database coupled to the at least one control circuit to the second local database. In one scenario, the plurality of urgency threshold values may be based on one or more inputs through a user interface operatively coupled to the at least one control circuit. Alternatively or in addition to, the at least one control circuit may access the first sensed data from the second local database. Alternatively or in addition to, the at least one control circuit may access the second sensed data from the second local database. Alternatively or in addition to, the at least one control circuit may determine a product item associated with at least one of: the first sensed data and the second sensed data. Alternatively or in addition to, the at least one control circuit may determine whether the at least one of: the first sensed data and the second sensed data has reached an urgency threshold value of the plurality of urgency threshold values. Alternatively or in addition to, the at least one control circuit may automatically initiate ordering and delivery of the product item when the urgency threshold value has been reached, wherein a mode of the delivery of the product item is based on the urgency threshold value. In one configuration, the system may include the remote database coupled to the at least one control circuit. By one approach, the remote database may store the plurality of urgency threshold values.

In some embodiments, a method for automatically ordering a product item associated with sensed data of a wearable portable user device includes determining, by at least one control circuit of a wearable portable user device, whether signaling data is received from at least one smart-device interface of the wearable portable user device at a first time. By one approach, the at least one smart-device interface may receive at least one of: the signaling data, default sensing exception data, and second sensed data associated with at least one smart device. By another approach, the method may include communicatively coupling the at least one control circuit with the at least one smart device in response to the determining that the signaling data is received. By another approach, the method may include prompting a user of the wearable portable user device to select whether a first local database of the wearable portable user device or a second local database of the at least one smart device stores a first sensed data from at least one first sensor of the wearable portable user device and the second sensed data associated with the at least one smart device in response to communicatively coupling the at least one control circuit with the at least one smart device. In one implementation, the method may include determining whether a previously stored data has been stored in the second local database for a time period at least equal to a threshold value in response to the user selecting the second local database of the at least one smart device. In one scenario, the method may include, in response to determining that the previously stored data has been stored in the second local database for the time period at least equal to the threshold value, deleting the previously stored data from the second local database. By yet another approach, the method may include copying a plurality of urgency threshold values from a remote database coupled to the at least one control circuit to the second local database, wherein the plurality of urgency threshold values is based on one or more inputs through a user interface operatively coupled to the at least one control circuit. In one configuration, the method may include accessing, by the at least one control circuit, the first sensed data. In another configuration, the method may include accessing, by the at least one control circuit, the second sensed data. Alternatively or in addition to, the method may include determining, by the at least one control circuit, a product item associated with at least one of: the first sensed data and the second sensed data. Alternatively or in addition to, the method may include determining, by the at least one control circuit, whether the at least one of: the first sensed data and the second sensed data has reached an urgency threshold value of the plurality of urgency threshold values. In one scenario, the plurality of urgency threshold values may be stored in the remote database. In yet another configuration, the method may include automatically initiating an order and delivery of the product item when the urgency threshold value has been reached, wherein a mode of the delivery of the item is based on the urgency threshold value.

To illustrate, FIGS. 1 through 9 are described below. FIG. 1 illustrates a simplified block diagram of an exemplary system 100 that automatically orders a product item associated with sensed data from one or more sensors 104 of at least one wearable portable user device 102. The system 100 includes at least one wearable portable user device 102. In one example, the wearable portable user device 102 may include any electronic devices that may be worn and/or on a user or a customer's person, such as but not limited to smart-glasses, smart-watch, and other such devices. By one approach, the wearable portable user device 102 may include one or more first sensors 104 and one or more local databases 106 (first local database(s) 106). In one configuration, the system 100 may include one or more smart-device interfaces 108. For example, a smart-device interface 108 may include Bluetooth adapter, WiFi adapter, wireless adapter, internet adapter, antenna, and/or any electronic interfaces and/or adapters that enable one electronic device to send and/or receive communications from another one or more electronic devices. By one approach, the wearable portable user device 102 may include at least one smart-device interface 108. By another approach, the smart-device interface 108 may be communicatively coupled to the wearable portable user device 102 via a communication network 122. In one example, the communication network 122 may include Bluetooth, WiFi, and Internet, among other types of communication networks providing communication medium between electronic devices (e.g., smartphones, laptops, computers, wearable portable user devices, smart devices, servers, etc.). By another approach, the wearable portable user device 102 may include a user interface 110. By another approach, the user interface 110 may be distinct from and/or communicatively coupled with the wearable portable user device 102 via the communication network 122.

In some embodiments, the system 100 may include one or more control circuits 118. By one approach, the control circuit 118 may be communicatively coupled with the wearable portable user device 102, the user interface 110, and/or the smart-device interface 108 via the communication network 122. In some embodiments, the wearable portable user device 102 may include the control circuit 118, the user interface 110, and the smart-device interface 108. In such an embodiment, the control circuit 118 may communicate to one or more smart devices 112 via the communication network 122 through the smart-device interface 108. In one example, the smart device 112 may include one or more second sensors 114 and one or more second local databases 116. In one configuration, the smart devices 112 may include any devices capable of coupling with, connected to, and/or communicating with other devices and/or networks via wireless and/or wired communication protocols (e.g., Bluetooth, WiFi, 3G, etc.) that operate interactively and/or autonomously. In another configuration, the sensors 104, 114 may include temperature sensors, heart rate sensors, pulse sensors, blood pressure sensors, brain sensors, displacement sensors, acceleration sensors, direction sensors, speed sensors, biosensors, chemical sensors, pressure sensors, position sensors, among other type of sensors whose data is used to determine well-being, physical status, and/or current condition of a user or a customer. Alternatively or in addition to, the system 100 may include one or more remote databases 120. By one approach, the remote database 120 may be coupled to the wearable portable user device 102 and/or the control circuit 118 via the communication network 122. In one example, the first local database 106, the second local database 116, and/or the remote database 120 may include memory devices (e.g., semiconductor memory). By one approach, the memory devices may include volatile memory, non-volatile memory, random access memory (RAM), read only memory (ROM), among other types of semiconductor memories capable of electronically storing data produced by electronic devices and/or sensor devices, to name a few.

In one configuration, at least one first sensor 104 may provide first sensed data of a user of the wearable portable user device 102. For example, the first sensed data may correspond the user's blood sugar level data. In one scenario, the user may participate in a triathlon competition. On the day of the competition, the user may be wearing the wearable portable user device 102. By one approach, the smart-device interface 108 of the wearable portable user device 102 may receive signaling data, default sensing exception data, and/or second sensed data associated with at least one smart device 112. For example, the first smart device 112 may include a smart-bicycle used by the user during the competition. In another example, the user may additionally carry his/her smartphone, the second smart device 112, be at a staging area or other location while still being in communication with the wearable portable user device. In one configuration, at a first time, the smart-device interface 108 may receive signaling data from a smart device 112 (e.g., the smart-bicycle and/or the smartphone) that is proximate and/or within a sensing distance of the wearable portable user device 102. In another configuration, a user may select to download an application to the wearable portable user device 102 and/or the smart device 112 to enable the wearable portable user device 102 and/or the smart device 112 to provide the signaling data to the control circuit 118 through the smart-device interface 108. By one approach, the control circuit 118 may periodically determine whether signaling data has been received at the smart-device interface 108. For example, the signaling data may include communication data and/or signal broadcasted by the smart device 112 and/or sensed by the wearable portable user device 102. In one scenario, in response to the determination that the signaling data is received, the control circuit 118 may communicatively couple with the smart device 112 via the smart-device interface 108. In such a scenario, the smart device 112 is also communicatively coupled to the wearable portable user device 102.

Alternatively or in addition to, in response to communicatively coupling with the at least one smart device, the control circuit 118 may prompt the user to select whether a first local database 106 of the wearable portable user device 102 or a second local database 116 of at least one smart device 112 stores the first sensed data from at least one first sensor 104 and the second sensed data from at least one second sensor 114 associated with the smart device 112. For example, when the user selects the second local database 116, sensor data provided by corresponding sensors 104, 114 of the smart device 112 and the wearable portable user device 102 are subsequently stored in the second local database 116. Similarly, the sensor data are subsequently stored in the first local database 106 when the user selects the first local database 106. For example, in response to the user selecting the second local database 116 of the smart device 112, the control circuit 118 may determine whether a previously stored data has been stored in the second local database 116 for a time period at least equal to a threshold value. In one scenario, to prevent running out of storage space, the control circuit 118 may perform data deletion in the second local database 116 based at least in part on how long the data has been stored in the second local database 116. For example, during an initial setup of the wearable portable user device 102, the user may preset that data stored in the local databases 106, 116 may be deleted when a time period from a first time the data is stored to a second time the control circuit 118 determines the age of the stored data is at least a threshold value (e.g., user may preset to delete stored data that are older than 3 days or any number of days and/or months). In such an example, in response to the determination that the previously stored data has been stored in the second local database 116 for the time period at least equal to the threshold value, the control circuit 118 may delete the previously stored data from the second local database 116. In another example, the user may modify the threshold value to another threshold value to change when stored data is deleted in the local databases 106, 116. For example, the stored data is deleted based on a timestamp associated with the stored data being greater than the another threshold value. By one approach, the deletion of stored data may occur when the control circuit 118 couples to the wearable portable user device 102 and/or the smart device 112.

Alternatively or in addition to, the control circuit 118 may copy a plurality of urgency threshold values from the remote database 120 to a local database (e.g., the first local database 106, the second local database 116, etc.) selected by a user. By one approach, the plurality of urgency threshold values may be based on one or more inputs through the user interface 110. In one scenario, the one or more inputs may include data associated with a user profile, preset values and/or data determined by the user, among other types of user inputs. For example, an urgency threshold value may include a value and/or a range of values. As such, the plurality of urgency threshold values may include a value, a range of values, or a combination thereof. In such an approach, an urgency threshold value is a value or a range of values that defines what action the control circuit 118 may take in response to the sensed data received from the wearable portable user device 102 and/or the smart device 112. Thus, the user predetermines one or more of the plurality of urgency threshold values and the corresponding action associated with each of the plurality of urgency threshold values that the control circuit 118 executes in response to receiving the sensed data. Alternatively or in addition to, the control circuit 118 may, in cooperation with the user's input, predetermine the plurality of urgency threshold values and the corresponding action. By one approach, the plurality of urgency threshold values may include a first value indicating a severe urgency instructing an automatic dispatch signal of an emergency medical service personnel to a location associated with the user, a second value indicating a high urgency instructing immediate delivery that is less than one day to the location, a third value indicating a medium urgency instructing at least one day or at least two days (e.g., at least 24 hours, at least 48 hours, or any combination of hours and minutes that is at least 24 hours or at least 48 hours) of delivery to the location, and/or a fourth value indicating a low urgency instructing no action.

In one implementation, the control circuit 118 may access the first sensed data from the second local database 116. Alternatively or in addition to, the control circuit 118 may access the second sensed data from the second local database 116. In another implementation, the control circuit 118 may determine a product item associated with the first sensed data and/or the second sensed data. By one approach, the product item may include a consumer product, a commercial product, a retail product, a military product, a non-commercial product, or any combination thereof). In another implementation, the control circuit 118 may determine whether the first sensed data and/or the second sensed data has reached an urgency threshold value of the plurality of urgency threshold values. For example, the user may preset and/or the remote database 120 may store associations of: sensed data with sensors and values corresponding to one or more product items, the values with corresponding urgency threshold values, and the urgency threshold values with modes of delivery of the corresponding one or more product items. In another example, a mode of the delivery of the product item may be based at least in part on cost of the delivery and/or distance to a delivery location. In such an example, a determination of a product item to deliver may be based at least in part on one or more inputs of the user through the user interface 110. In another example, the control circuit 118 may determine that a first combination of a first sensed data corresponding to a first value and a second sensed data corresponding to a second value is associated with a first product item based on stored associations in the remote database 120 and/or the user selected local database (e.g., the first local database 106 or the second local database 116). Additionally, the control circuit 118 may determine that the first combination of the first value and the second value is additionally associated with a second urgency threshold value indicating a high urgency instructing immediate delivery that is less than one day (e.g., less than 24 hours, an hour, any number of hours less than 24 hours, less than 60 minutes, or any combination thereof) to a location associated with a user of the wearable portable user device 102 and/or the smart device 112. For example, the control circuit 118 may determine that based on the received sensing data, the user has been wearing the wearable portable user device 102 and/or in proximity or sensing distance of the smart device 112 from an initial time the control circuit 118 has initially sensed the user. In another example, once the wearable portable user device 102 and/or the smart device 112 are paired with a particular user, the control circuit 118 may authenticate received sensor data based on a continuous and/or uninterrupted sensing of the user within a threshold by at least one of the first sensor 104 and the second sensor 114. In another example, in addition to determining that the user has been wearing the wearable portable user device 102 and/or the smart device 112 for a period of time and/or within a threshold of arrival of a delivered product item, the control circuit 118 may determine and/or authenticate that the user is authorized to receive the delivery. In another configuration, the associations stored in the remote database 120 may be copied by the control circuit 118 to a local database selected by the user, for example, the second local database 116. Alternatively or in addition to, the control circuit 118 may automatically initiate ordering and delivery of a corresponding product item determined by the control circuit 118 when an urgency threshold value has been reached based on an access of the control circuit 118 to determine an action to execute based on matching the combinations of values, as illustrated above, with the stored associations of the remote database 120 and/or the local database selected by the user, for example, the second local database 116.

In another illustrative non-limiting example, in determining whether a particular urgency threshold value has been reached, the control circuit 118 may determine a particular combination of a first sensed data from the wearable portable user device 102 and a second sensed data from the smart device 112. In one example, when there is no smart device 112 that is coupled with the control circuit 118, the control circuit 118 may only determine the particular combination of the first sensed data with a null or do no care value associated with the second sensed data. By one approach, the control circuit 118 may access the remote database 120 and/or a user selected local database (e.g., the first local database 106 or the second local database 116) and find a corresponding urgency threshold value based on a match of the particular combination with a particular association of the first sensed data and the second sensed data stored in the remote database 120 and/or the user selected local database. Alternatively or in addition to, the control circuit 118 may perform a match starting with a highest level of urgency and ending with a lowest level of urgency. For example, control circuit 118 may perform a match initially with an urgency threshold value that corresponds to a highest level of urgency and finally with an urgency threshold value that corresponds to a lowest level of urgency. In such an approach, the control circuit 118 may determine whether the first sensed data and/or the second sensed data has reached a second urgency threshold value of a plurality of urgency threshold values stored in the remote database 120 and/or a user selected local database (e.g., the first local database 106 or the second local database 116). In one configuration, the control circuit 118 may provide an automatic dispatch signal to an emergency medical service personnel when the second urgency threshold has been reached. Alternatively or in addition to, the control circuit 118 may determine no action to be executed by the control circuit 118 when the second urgency threshold value has been reached in response to a combination of the first sensed data and the second sensed data. Alternatively or in addition to, the control circuit 118 may determine whether the user of the wearable portable user device 102 is at a retail store or en route to the retail store based on location data provided by one of the first sensors 104. In one configuration, the control circuit 118 may, in response to the determination that the user is at the retail store or en route to the retail store, add a product item, determined by the control circuit 118, to a shopping list associated with the user when the urgency threshold value has been reached instead of automatic ordering and delivery of the product item.

In some embodiments, the user interface 110 may receive a first input of one or more inputs from a user. By one approach, the first input may correspond to a goal that the user associates with a receipt of a first sensed data associated with the wearable portable user device 102 and/or a second sensed data associated with the smart device 112. In such an approach, in receiving the first input, the control circuit 118 may associate the first input with a combination of the first sensed data and the second sensed data and initiate storage of the association in the remote database 120. Alternatively or in addition to, the control circuit 118 may receive a second input from the user corresponding to an urgency threshold value to be associated with the goal. By one approach, in response to the second input, the control circuit 118 may associate the combination with the urgency threshold value and/or the goal and initiate storage of the association in the remote database 120.

In some embodiments, the control circuit 118 may determine whether the first sensed data and/or the second sensed data is associated with an automated variable dosing prescription defined by a doctor of the user. For example, the automated variable dosing prescription may be a function of a doctor prescribed dosing limits particular to the user. In one implementation, the remote database 120 and/or a user selected local database (e.g., the first local database 106 or the second local database 116) may store associations of each of the doctor prescribed dosing limits with combinations of the first sensed data and the second sensed data. Alternatively or in addition to, the remote database 120 and/or a user selected local database (e.g., the first local database 106 or the second local database 116) may further store associations of the combinations with corresponding plurality of urgency threshold values and/or with combinations of one or more urgency threshold values. In another illustrative non-limiting example, an automatic initiation of ordering and delivery of a product item may be based at least in part on: a determination that a first sensed data and/or a second sensed data is associated with an automated variable dosing prescription based on an access by the control circuit 118 of associations stored in the remote database 120 and/or the user selected local database (e.g., the first local database 106 or the second local database 116), a determination that the first sensed data and/or the second sensed data has reached an urgency threshold value, and/or a determination that the first sensed data and/or the second sensed data is less than an urgency threshold value. In one configuration, in response to the determination that the first sensed data and/or the second sensed data is associated with the automated variable dosing prescription and that the first sensed data and/or the second sensed data has reached a first urgency threshold value but less than a second urgency threshold value, the control circuit 118 may modify an initial dosage prescribed by the doctor to the user based on an automated variable dosing prescription and the first sensed data and/or the second sensed data. In an illustrative non-limiting example, the first urgency threshold value may be associated with no action to be executed by the control circuit 118 and the second urgency threshold value may be associated with automatically calling an emergency medical service personnel. In such an example, when the control circuit 118 determines that a combination of a first sensed data from a first sensor 104 of the wearable portable user device 102 and a second sensed data from a second sensor 114 of the smart device 112 correspond to an urgency threshold value that is greater than the first urgency threshold value but less than the second urgency threshold value, the control circuit 118 may modify an initial dosage or a previously doctor prescribed dosage to the user. For example, the control circuit 118 may send a message to a display device associated with the wearable portable user device 102 indicating that the user should start taking a higher dosage equal to one of the predetermined dosage amount stored in the remote database 120 and/or a user selected local database (e.g., the first local database 106 or the second local database 116). Alternatively or in addition to, in automatically initiating an order and delivery of a product item, the control circuit 118 may provide the modified initial dosage to a pharmacy associate. Alternatively or in addition to, the control circuit 118 may subsequently and/or automatically submit an order of a product item determined by the control circuit 118 to a retail store associated with the pharmacy associate. For example, the product item may correspond to a refill of a prescription associated with the user based on the modified initial dosage. By one approach, the control circuit 118 may notify the user via the user interface 110 and/or a display associated with the wearable portable user device 102 when the refill is complete and/or the product item is ready for automatic delivery to a destination location associated with and/or selected by the user. In continuing the illustrative non-limiting example above, the control circuit 118 may determine, based on the first sensed data (e.g., elevated heart rate) provided by the first sensor 104 of the wearable portable user device 102 worn or on the user's person and the second sensed data (e.g., decreased in bicycle speed) provided by the second sensor 114 of the smart bicycle used by the user in a triathlon competition, that the user is requiring rehydration. As such, the control circuit 118 may, based on a combination of the elevated heart rate and the decreased in bicycle speed and an association of at least one rehydrating product (e.g., a bottle of Gatorade) in the remote database 120 and/or a user selected local database (e.g., the first local database 106 or the second local database 116), automatically submit an order and delivery for at least one rehydrating product. Alternatively or in addition to, the control circuit 118 may determine that the combination is associated with an automated variable dosing prescription predetermined by a doctor and/or by the control circuit 118 based on a doctor prescribed formula stored in the remote database 120 and/or a user selected local database 106,116. Alternatively or in addition to, the control circuit 118 may determine that the combination is associated with an automated variable dosing prescription based on associations stored in the remote database 120 and/or a user selected local database 106,116. Alternatively or in addition to, the control circuit 118 may determine that the combination is associated with an urgency threshold value that falls between a first urgency threshold value (e.g., indicating no action) and a second urgency threshold value (e.g., indicating dispatch of an emergency medical service personnel). As such, the control circuit 118 may modify a previously doctor prescribed dosage to a dosage value based on the automated variable dosing prescription predetermined by the doctor and/or provide the modified initial dosage to a pharmacy associate.

In some embodiments, prior to executing any actions in response to a combination of a first sensed data from the wearable portable user device 102 and a second sensed data from the smart device 112 as illustrated above, the control circuit 118 may determine whether the first sensed data and/or the second sensed data is at least a threshold from an average sensed data determined from historical sensed data received by the control circuit 118 over a time period. For example, each time sensed data is received from the wearable portable user device 102 and/or the smart device 112, the received sensed data is stored in a user selected local database (e.g., the first local database 106 or the second local database 116). By one approach, the control circuit 118 may calculate an average sensed data from the stored sensed data received over a time period (e.g., historical sensed data). In one configuration, the control circuit 118 may automatically initiate an order and a delivery of a product item based in part on a determination that the first sensed data and the second sensed data is at least a threshold from the average sensed data. Alternatively, the control circuit 118 may cancel an automatic initiation of ordering and delivery of a product item based on a determination that the first sensed data and the second sensed data is at least a threshold from the average sensed data. In some embodiments, the control circuit 118 may periodically determine, at a second time, whether signaling data is received from the smart-device interface 108. For example, the control circuit 118 may receive the signaling data when the smart device 112 is in proximity to the wearable portable user device 102 worn or on the user's person. By one approach, the control circuit 118 may receive a default sensing exception data when at least one of the smart devices 112 determines that an abnormal event affecting a user of the wearable portable user device 102 and/or the smart device 112 occurred. For example, the second sensor 114 may provide data to the smart device 112 and/or the control circuit 118 indicating that the bicycle used by the user during a triathlon competition abruptly reduced speed to zero speed. In another example, an abnormal event may include any events and/or a combination of events that are associated with sensor data received from the wearable portable user device 102 and/or the smart device 112, where the sensor data are outside one or more predetermined thresholds defining a normal event.

In one scenario, the one or more predetermined thresholds may be determined by the user, a manufacturer of the wearable portable user device 102 and/or the smart device 112, and/or based in part on industry standard, among other sources capable of providing thresholds to be associated with sensor data output by the wearable portable user device 102 and/or the smart device 112.

Figure 2A:
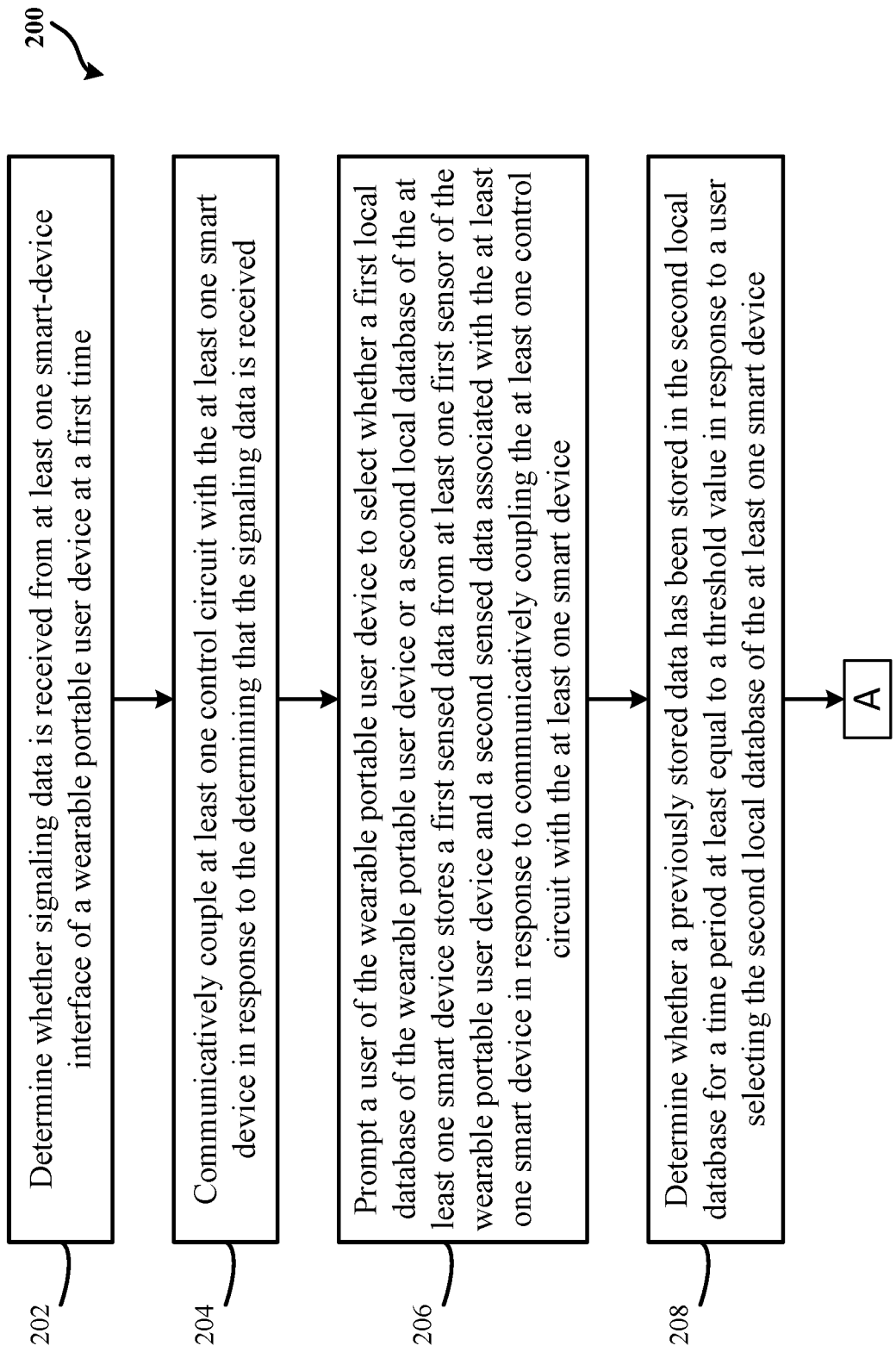
FIGS. 2A-B shows a flow diagram of an exemplary process of automatically ordering a product item in accordance with some embodiments.
Figure 2B:
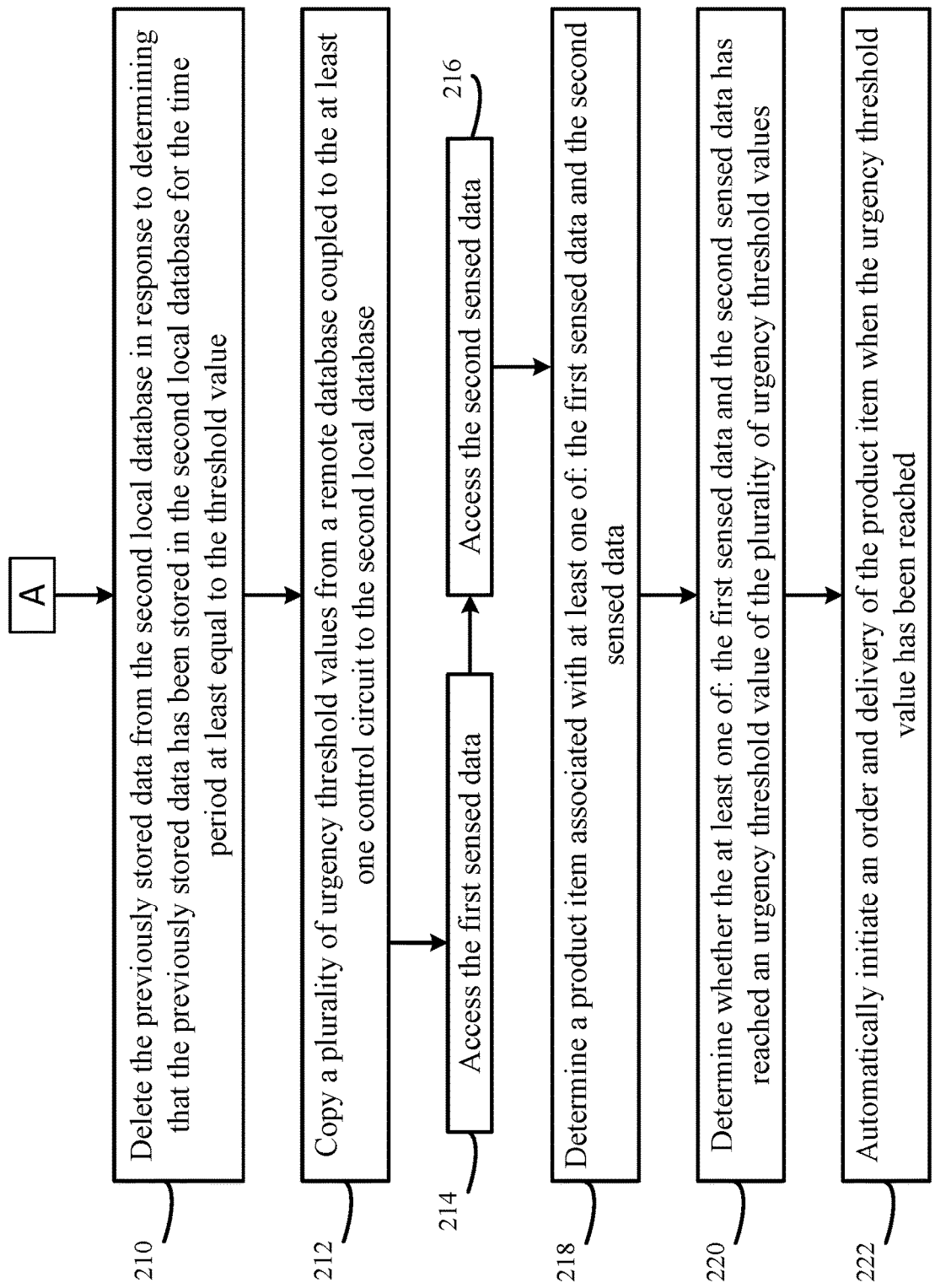

FIGS. 2A-2B illustrate flow diagrams of an exemplary method 200 for automatically ordering a product item associated with sensed data of a wearable portable user device. The exemplary method 200 may be implemented in the system 100 of FIG. 1. One or more steps in the method 200 may be implemented in the wearable portable user device 102, the control circuit 118, the remote database 120, the first local database 106, the second local database 116, and/or the smart device 112 of FIG. 1. The method 200 includes, at step 202, determining, by at least one control circuit of a wearable portable user device, whether signaling data is received from at least one smart-device interface of the wearable portable user device at a first time. By one approach, the at least one smart-device interface is configured to receive at least one of: the signaling data, default sensing exception data, and second sensed data associated with at least one smart device. In one configuration, the method 200 may include, at step 204, communicatively coupling the at least one control circuit with the at least one smart-device in response to the determining that the signaling data is received. In another configuration, the method 200 may include, at step 206, prompting a user of the wearable portable user device to select whether a first local database of the wearable portable user device or a second local database of the at least one smart device stores a first sensed data from at least one first sensor of the wearable portable user device and the second sensed data associated with the at least one smart device in response to communicatively coupling the at least one control circuit with the at least one smart device. In another configuration, the method 200 may include determining whether a previously stored data has been stored in the second local database for a time period at least equal to a threshold value in response to the user selecting the second local database of the at least one smart device, at step 208. Alternatively or in addition, the method 200 may include deleting the previously stored data from the second local database in response to determining that the previously stored data has been stored in the second local database for the time period at least equal to the threshold value, at step 210. By one approach, the method 200 may include, at step 212, copying a plurality of urgency threshold values from a remote database coupled to the at least one control circuit to the second local database. In one example, the plurality of urgency threshold values may be based on one or more inputs through a user interface operatively coupled to the at least one control circuit. Alternatively or in addition, the method 200 may include accessing, by the at least one control circuit, the first sensed data, at step 214. Alternatively or in addition, the method 200 may include accessing, by the at least one control circuit, the second sensed data, at step 216. By one approach, the method 200 may include, at step 218, determining, by the at least one control circuit, a product item associated with at least one of: the first sensed data and the second sensed data. By another approach, the method 200 may include, at step 220, determining, by the at least one control circuit, whether the at least one of: the first sensed data and the second sensed data has reached an urgency threshold value of the plurality of urgency threshold values. In one example, the plurality of urgency threshold values may be stored in the remote database. Alternatively or in addition, the method 200 may include, at step 222, automatically initiating an order and delivery of the product item when the urgency threshold value has been reached. In one example, a mode of the delivery of the item may be based on the urgency threshold value.

In some embodiments, the method 200 may include determining whether the at least one of: the first sensed data and the second sensed data has reached a second urgency threshold value of the plurality of urgency threshold values. Alternatively or in addition to, the method 200 may include providing an automatic dispatch signal to an emergency medical service personnel when the second urgency threshold has been reached. In one implementation, the method 200 may include determining whether the at least one of: the first sensed data and the second sensed data has reached a second urgency threshold value of the plurality of urgency threshold values. Alternatively or in addition to, the method 200 may include determining no action when the second urgency threshold value has been reached. In another implementation, the method 200 may include determining whether the user of the portable user device is at a retail store or en route to the retail store. Alternatively or in addition to, the method 200 may include, in response to the determining that the user is at the retail store or en route to the retail store, adding the product item to a shopping list associated with the user when the urgency threshold value has been reached instead of the automatically initiating the order and delivery of the product item. By one approach, the method 200 may include determining whether the at least one of: the first sensed data and the second sensed data is associated with an automated variable dosing prescription defined by a doctor of the user. In one example, the automated variable dosing prescription may be a function of a doctor prescribed dosing limits particular to the user. In another example, automatically initiating the order and delivery of the product item may be further based on the determining that the at least one of: the first sensed data and the second sensed data is associated with the automated variable dosing prescription, the determining that the at least one of: the first sensed data and the second sensed data has reached the urgency threshold value, and/or determining that the at least one of: the first sensed data and the second sensed data is less than a second urgency threshold value of the plurality of urgency threshold values. Alternatively or in addition to, the method 200 may include, in response to the determining that the at least one of: the first sensed data and the second sensed data is associated with the automated variable dosing prescription and the determining that the at least one of: the first sensed data and the second sensed data has reached the urgency threshold value but less than the second urgency threshold value, modifying an initial dosage prescribed by the doctor to the user based on the at least one of: the first sensed data and the second sensed data and the automated variable dosing prescription. In some embodiments, the method 200 including automatically initiating the order and delivery of the product item, may further include providing the modified initial dosage to a pharmacy associate. Alternatively or in addition to, in such an embodiment, the method 200 may include ordering the product item. By one approach, the product item may correspond to a refill of a prescription associated with the user based on the modified initial dosage. Alternatively or in addition to, the method 200 may include notifying the user via a user interface coupled to the portable user device when the refill is complete, and the product item is ready for an automatic delivery to a destination location associated with the user.

In some embodiments, the method 200 may include determining whether the at least one of: the first sensed data and the second sensed data is at least a threshold from an average sensed data determined from historical sensed data received by the at least one control circuit over a time period in response to the determining that the at least one of: the first sensed data and the second sensed data is associated with the automated variable dosing prescription but prior to the determining that the at least one of: the first sensed data and the second sensed data has reached the urgency threshold value but less than the second urgency threshold value. By one approach, the method 200 may include cancelling the automatically initiating the order and delivery of the product item based on the determining that the at least one of: the first sensed data and the second sensed data is at least the threshold from the average sensed data. In one implementation, the method 200 may include determining whether the signaling data is received from the at least one smart-device interface at a second time. In one configuration, the method 200 may include receiving the default sensing exception data when the at least one smart device determines that an abnormal event affecting the user occurred. In another configuration, the method 200 may include initiating receipts of the second sensed data and the first sensed data at the second time in response to the receiving of the default sensing exception data. By one approach, the method 200 may include automatically initiating one or more predetermined action responses based on the second sensed data and the first sensed data received at the second time. By another approach, the method 200 may include initiating storage of the second sensed data and the first sensed data to the remote database.

Further, the circuits, circuitry, systems, devices, processes, methods, techniques, functionality, services, servers, sources and the like described herein may be utilized, implemented and/or run on many different types of devices and/or systems. FIG. 3 illustrates an exemplary system 300 that may be used for implementing any of the components, circuits, circuitry, systems, functionality, apparatuses, processes, or devices of the system 100 of FIG. 1, the method 200 of FIGS. 2A-2B, and/or other above or below mentioned systems or devices, or parts of such circuits, circuitry, functionality, systems, apparatuses, processes, or devices. For example, the system 300 may be used to implement some or all of the system for automatically ordering a product item associated with sensed data from at least one sensor 104 of the wearable portable user device 102, the wearable portable user device 102, the control circuit 118, the remote database 120, the smart device 112, and/or other such components, circuitry, functionality and/or devices. However, the use of the system 300 or any portion thereof is certainly not required.

By way of example, the system 300 may comprise a processor module (or a control circuit) 312, memory 314, and one or more communication links, paths, buses or the like 318. Some embodiments may include one or more user interfaces 316, and/or one or more internal and/or external power sources or supplies 340. The control circuit 312 can be implemented through one or more processors, microprocessors, central processing unit, logic, local digital storage, firmware, software, and/or other control hardware and/or software, and may be used to execute or assist in executing the steps of the processes, methods, functionality and techniques described herein, and control various communications, decisions, programs, content, listings, services, interfaces, logging, reporting, etc. Further, in some embodiments, the control circuit 312 can be part of control circuitry and/or a control system 310, which may be implemented through one or more processors with access to one or more memory 314 that can store instructions, code and the like that is implemented by the control circuit and/or processors to implement intended functionality. In some applications, the control circuit and/or memory may be distributed over a communications network (e.g., LAN, WAN, Internet) providing distributed and/or redundant processing and functionality. Again, the system 300 may be used to implement one or more of the above or below, or parts of, components, circuits, systems, processes and the like. For example, the system 300 may implement the system 100 for automatically ordering a product item with the control circuit 118 being the control circuit 312.

The user interface 316 can allow a user to interact with the system 300 and receive information through the system. In some instances, the user interface 316 includes a display 322 and/or one or more user inputs 324, such as buttons, touch screen, track ball, keyboard, mouse, etc., which can be part of or wired or wirelessly coupled with the system 300. Typically, the system 300 further includes one or more communication interfaces, ports, transceivers 320 and the like allowing the system 300 to communicate over a communication bus, a distributed computer and/or communication network (e.g., a local area network (LAN), the Internet, wide area network (WAN), etc.), communication link 318, other networks or communication channels with other devices and/or other such communications or combination of two or more of such communication methods. Further the transceiver 320 can be configured for wired, wireless, optical, fiber optical cable, satellite, or other such communication configurations or combinations of two or more of such communications. Some embodiments include one or more input/output (I/O) interface 334 that allow one or more devices to couple with the system 300. The I/O interface can be substantially any relevant port or combinations of ports, such as but not limited to USB, Ethernet, or other such ports. The I/O interface 334 can be configured to allow wired and/or wireless communication coupling to external components. For example, the I/O interface can provide wired communication and/or wireless communication (e.g., Wi-Fi, Bluetooth, cellular, RF, and/or other such wireless communication), and in some instances may include any known wired and/or wireless interfacing device, circuit and/or connecting device, such as but not limited to one or more transmitters, receivers, transceivers, or combination of two or more of such devices.

In some embodiments, the system may include one or more sensors 326 to provide information to the system and/or sensor information that is communicated to another component, such as the wearable portable user device(s) 102, the control circuit(s) 118, the remote database(s) 120, the smart device(s) 112, etc. The sensors can include substantially any relevant sensor, such as temperature sensors, biometric sensors, distance measurement sensors (e.g., optical units, sound/ultrasound units, etc.), optical-based scanning sensors to sense and read optical patterns (e.g., bar codes), radio frequency identification (RFID) tag reader sensors capable of reading RFID tags in proximity to the sensor, and other such sensors. The foregoing examples are intended to be illustrative and are not intended to convey an exhaustive listing of all possible sensors. Instead, it will be understood that these teachings will accommodate sensing any of a wide variety of circumstances in a given application setting.

The system 300 comprises an example of a control and/or processor-based system with the control circuit 312. Again, the control circuit 312 can be implemented through one or more processors, controllers, central processing units, logic, software and the like. Further, in some implementations the control circuit 312 may provide multiprocessor functionality.

The memory 314, which can be accessed by the control circuit 312, typically includes one or more processor-readable and/or computer-readable media accessed by at least the control circuit 312, and can include volatile and/or nonvolatile media, such as RAM, ROM, EEPROM, flash memory and/or other memory technology. Further, the memory 314 is shown as internal to the control system 310; however, the memory 314 can be internal, external or a combination of internal and external memory. Similarly, some or all of the memory 314 can be internal, external or a combination of internal and external memory of the control circuit 312. The external memory can be substantially any relevant memory such as, but not limited to, solid-state storage devices or drives, hard drive, one or more of universal serial bus (USB) stick or drive, flash memory secure digital (SD) card, other memory cards, and other such memory or combinations of two or more of such memory, and some or all of the memory may be distributed at multiple locations over the computer network. The memory 314 can store code, software, executables, scripts, data, content, lists, programming, programs, log or history data, user information, customer information, product information, and the like. While FIG. 3 illustrates the various components being coupled together via a bus, it is understood that the various components may actually be coupled to the control circuit and/or one or more other components directly. In some embodiments, an automatic ordering and/or delivery of product items by the wearable portable user device 102 and/or the smart device 112 may be authorized and/or authenticated at least in part through the use of blockchain technology. Alternatively or in addition to, the communication network 122 may include a blockchain network. Blockchain technology is further described in paragraphs below.

Descriptions of some embodiments of blockchain technology are provided with reference to FIG. 4-9 herein. In some embodiments of the invention described above, blockchain technology may be utilized to record sales record, delivery record, transactions, etc. One or more of the smart devices, user devices, wearable devices, sensors, databases, and/or control circuits described herein may comprise a node in a distributed blockchain system storing a copy of the blockchain record. Updates to the blockchain may comprise transfer of product items, sales, delivery, data updates, new data and one or more nodes on the system may be configured to incorporate one or more updates into blocks to add to the distributed database.

Distributed database and shared ledger database generally refer to methods of peer-to-peer record keeping and authentication in which records are kept at multiple nodes in the peer-to-peer network instead of kept at a trusted party. A blockchain may generally refer to a distributed database that maintains a growing list of records in which each block contains a hash of some or all previous records in the chain to secure the record from tampering and unauthorized revision. A hash generally refers to a derivation of original data. In some embodiments, the hash in a block of a blockchain may comprise a cryptographic hash that is difficult to reverse and/or a hash table. Blocks in a blockchain may further be secured by a system involving one or more of a distributed timestamp server, cryptography, public/private key authentication and encryption, proof standard (e.g. proof-of-work, proof-of-stake, proof-of-space), and/or other security, consensus, and incentive features. In some embodiments, a block in a blockchain may comprise one or more of a data hash of the previous block, a timestamp, a cryptographic nonce, a proof standard, and a data descriptor to support the security and/or incentive features of the system.

In some embodiments, a blockchain system comprises a distributed timestamp server comprising a plurality of nodes configured to generate computational proof of record integrity and the chronological order of its use for content, trade, and/or as a currency of exchange through a peer-to-peer network. In some embodiments, when a blockchain is updated, a node in the distributed timestamp server system takes a hash of a block of items to be timestamped and broadcasts the hash to other nodes on the peer-to-peer network. The timestamp in the block serves to prove that the data existed at the time in order to get into the hash. In some embodiments, each block includes the previous timestamp in its hash, forming a chain, with each additional block reinforcing the ones before it. In some embodiments, the network of timestamp server nodes performs the following steps to add a block to a chain: 1) new activities are broadcasted to all nodes, 2) each node collects new activities into a block, 3) each node works on finding a difficult proof-of-work for its block, 4) when a node finds a proof-of-work, it broadcasts the block to all nodes, 5) nodes accept the block only if activities are authorized, and 6) nodes express their acceptance of the block by working on creating the next block in the chain, using the hash of the accepted block as the previous hash. In some embodiments, nodes may be configured to consider the longest chain to be the correct one and work on extending it. A digital currency implemented on a blockchain system is described by Satoshi Nakamoto in "Bitcoin: A Peer-to-Peer Electronic Cash System" (http://bitcoin.org/bitcoin.pdf), the entirety of which is incorporated herein by reference.

Figure 4:
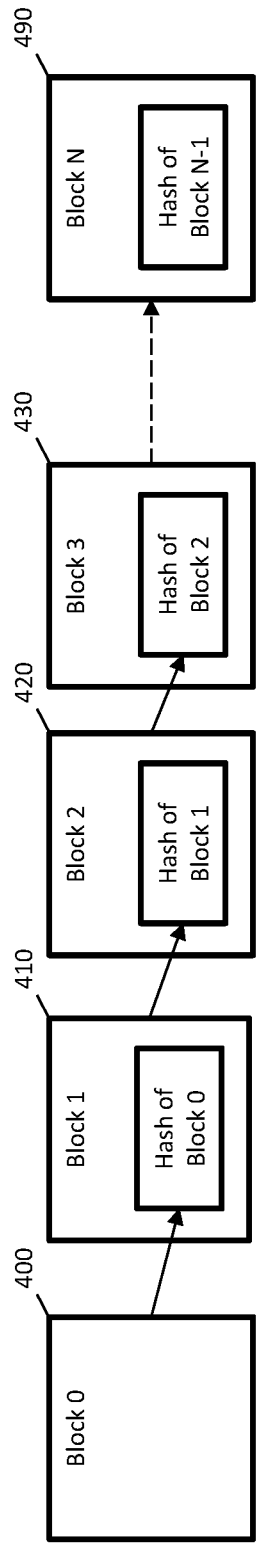
FIG. 4 comprises an illustration of blocks as configured in accordance with various embodiments of these teachings.

Now referring to FIG. 4, an illustration of a blockchain according to some embodiments is shown. In some embodiments, a blockchain comprises a hash chain or a hash tree in which each block added in the chain contains a hash of the previous block. In FIG. 4, block 0 400 represents a genesis block of the chain. Block 1 410 contains a hash of block 0 400, block 2 420 contains a hash of block 1 410, block 3 430 contains a hash of block 2 420, and so forth. Continuing down the chain, block N contains a hash of block N−1. In some embodiments, the hash may comprise the header of each block. Once a chain is formed, modifying or tampering with a block in the chain would cause detectable disparities between the blocks. For example, if block 1 is modified after being formed, block 1 would no longer match the hash of block 1 in block 2. If the hash of block 1 in block 2 is also modified in an attempt to cover up the change in block 1, block 2 would not then match with the hash of block 2 in block 3. In some embodiments, a proof standard (e.g. proof-of-work, proof-of-stake, proof-of-space, etc.) may be required by the system when a block is formed to increase the cost of generating or changing a block that could be authenticated by the consensus rules of the distributed system, making the tampering of records stored in a blockchain computationally costly and essentially impractical. In some embodiments, a blockchain may comprise a hash chain stored on multiple nodes as a distributed database and/or a shared ledger, such that modifications to any one copy of the chain would be detectable when the system attempts to achieve consensus prior to adding a new block to the chain. In some embodiments, a block may generally contain any type of data and record. In some embodiments, each block may comprise a plurality of transaction and/or activity records.

In some embodiments, blocks may contain rules and data for authorizing different types of actions and/or parties who can take action. In some embodiments, transaction and block forming rules may be part of the software algorithm on each node. When a new block is being formed, any node on the system can use the prior records in the blockchain to verify whether the requested action is authorized. For example, a block may contain a public key of an owner of an asset that allows the owner to show possession and/or transfer the asset using a private key. Nodes may verify that the owner is in possession of the asset and/or is authorized to transfer the asset based on prior transaction records when a block containing the transaction is being formed and/or verified. In some embodiments, rules themselves may be stored in the blockchain such that the rules are also resistant to tampering once created and hashed into a block. In some embodiments, the blockchain system may further include incentive features for nodes that provide resources to form blocks for the chain. For example, in the Bitcoin system, "miners' are nodes that compete to provide proof-of-work to form a new block, and the first successful miner of a new block earns Bitcoin currency in return.

Figure 5:
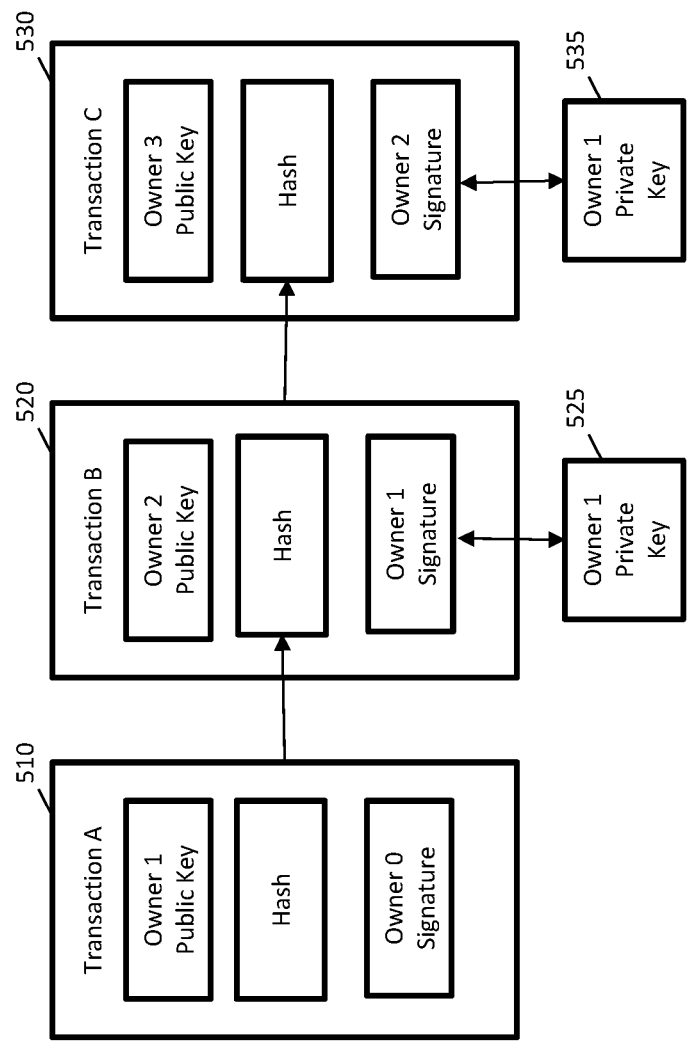
FIG. 5 comprises an illustration of transactions configured in accordance with various embodiments of these teachings.

Now referring to FIG. 5, an illustration of blockchain-based transactions according to some embodiments is shown. In some embodiments, the blockchain illustrated in FIG. 5 comprises a hash chain protected by private/public key encryption. Transaction A 510 represents a transaction recorded in a block of a blockchain showing that owner 1 (recipient) obtained an asset from owner 0 (sender). Transaction A 510 contains owner's 1 public key and owner 0's signature for the transaction and a hash of a previous block. When owner 1 transfers the asset to owner 2, a block containing transaction B 520 is formed. The record of transaction B 520 comprises the public key of owner 2 (recipient), a hash of the previous block, and owner 1's signature for the transaction that is signed with the owner 1's private key 525 and verified using owner 1's public key in transaction A 510. When owner 2 transfers the asset to owner 3, a block containing transaction C 530 is formed. The record of transaction C 530 comprises the public key of owner 3 (recipient), a hash of the previous block, and owner 2's signature for the transaction that is signed by owner 2's private key 535 and verified using owner 2's public key from transaction B 520. In some embodiments, when each transaction record is created, the system may check previous transaction records and the current owner's private and public key signature to determine whether the transaction is valid. In some embodiments, transactions are being broadcasted in the peer-to-peer network and each node on the system may verify that the transaction is valid prior to adding the block containing the transaction to their copy of the blockchain. In some embodiments, nodes in the system may look for the longest chain in the system to determine the most up-to-date transaction record to prevent the current owner from double spending the asset. The transactions in FIG. 5 are shown as an example only. In some embodiments, a blockchain record and/or the software algorithm may comprise any type of rules that regulate who and how the chain may be extended. In some embodiments, the rules in a blockchain may comprise clauses of a smart contract that is enforced by the peer-to-peer network.

Figure 6:
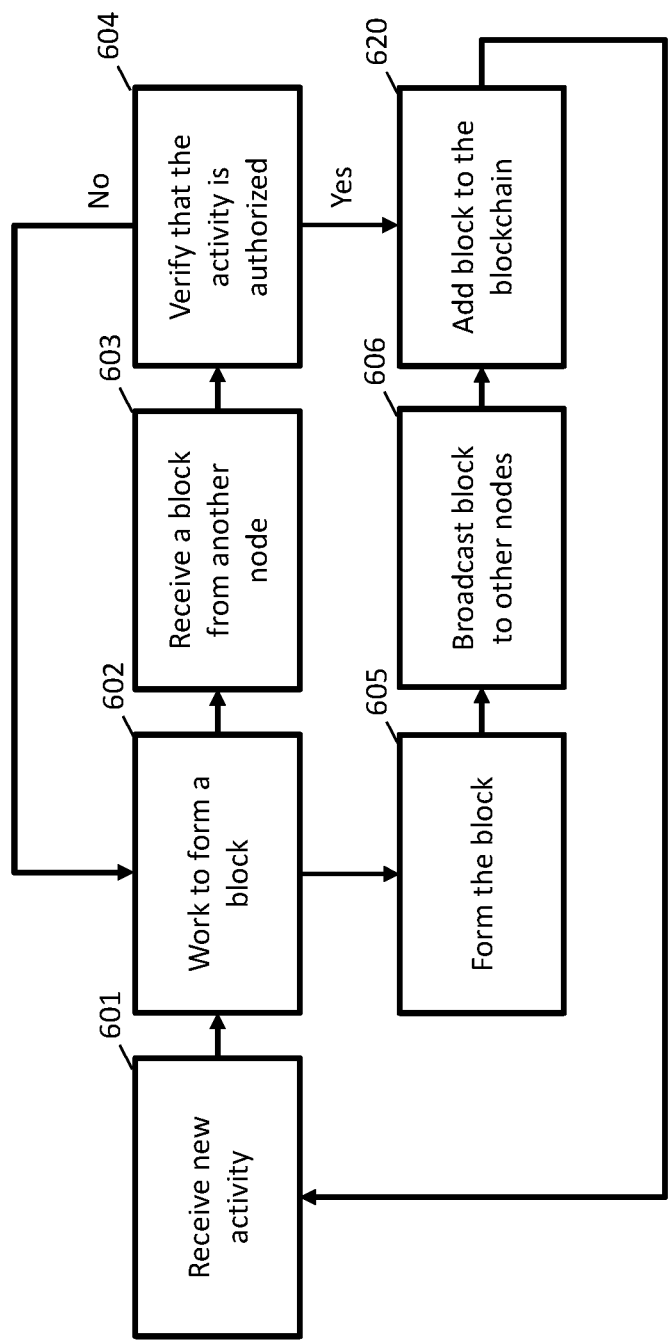
FIG. 6 comprises a flow diagram in accordance with various embodiments of these teachings.

Now referring to FIG. 6, a flow diagram according to some embodiments is shown. In some embodiments, the steps shown in FIG. 6 may be performed by a processor-based device, such as a computer system, a server, a distributed server, a timestamp server, a blockchain node, and the like. In some embodiments, the steps in FIG. 6 may be performed by one or more of the nodes in a system using blockchain for record keeping.

In step 601, a node receives a new activity. The new activity may comprise an update to the record being kept in the form of a blockchain. In some embodiments, for blockchain supported digital or physical asset record keeping, the new activity may comprise an asset transaction. In some embodiments, the new activity may be broadcasted to a plurality of nodes on the network prior to step 601. In step 602, the node works to form a block to update the blockchain. In some embodiments, a block may comprise a plurality of activities or updates and a hash of one or more previous block in the blockchain. In some embodiments, the system may comprise consensus rules for individual transactions and/or blocks and the node may work to form a block that conforms to the consensus rules of the system. In some embodiments, the consensus rules may be specified in the software program running on the node. For example, a node may be required to provide a proof standard (e.g. proof of work, proof of stake, etc.) which requires the node to solve a difficult mathematical problem for form a nonce in order to form a block. In some embodiments, the node may be configured to verify that the activity is authorized prior to working to form the block. In some embodiments, whether the activity is authorized may be determined based on records in the earlier blocks of the blockchain itself.

After step 602, if the node successfully forms a block in step 605 prior to receiving a block from another node, the node broadcasts the block to other nodes over the network in step 606. In some embodiments, in a system with incentive features, the first node to form a block may be permitted to add incentive payment to itself in the newly formed block. In step 620, the node then adds the block to its copy of the blockchain. In the event that the node receives a block formed by another node in step 603 prior to being able to form the block, the node works to verify that the activity recorded in the received block is authorized in step 604. In some embodiments, the node may further check the new block against system consensus rules for blocks and activities to verify whether the block is properly formed. If the new block is not authorized, the node may reject the block update and return to step 602 to continue to work to form the block. If the new block is verified by the node, the node may express its approval by adding the received block to its copy of the blockchain in step 620. After a block is added, the node then returns to step 601 to form the next block using the newly extended blockchain for the hash in the new block.

In some embodiments, in the event one or more blocks having the same block number is received after step 620, the node may verify the later arriving blocks and temporarily store these blocks if they pass verification. When a subsequent block is received from another node, the node may then use the subsequent block to determine which of the plurality of received blocks is the correct/consensus block for the blockchain system on the distributed database and update its copy of the blockchain accordingly. In some embodiments, if a node goes offline for a time period, the node may retrieve the longest chain in the distributed system, verify each new block added since it has been offline, and update its local copy of the blockchain prior to proceeding to step 601.

Figure 7:
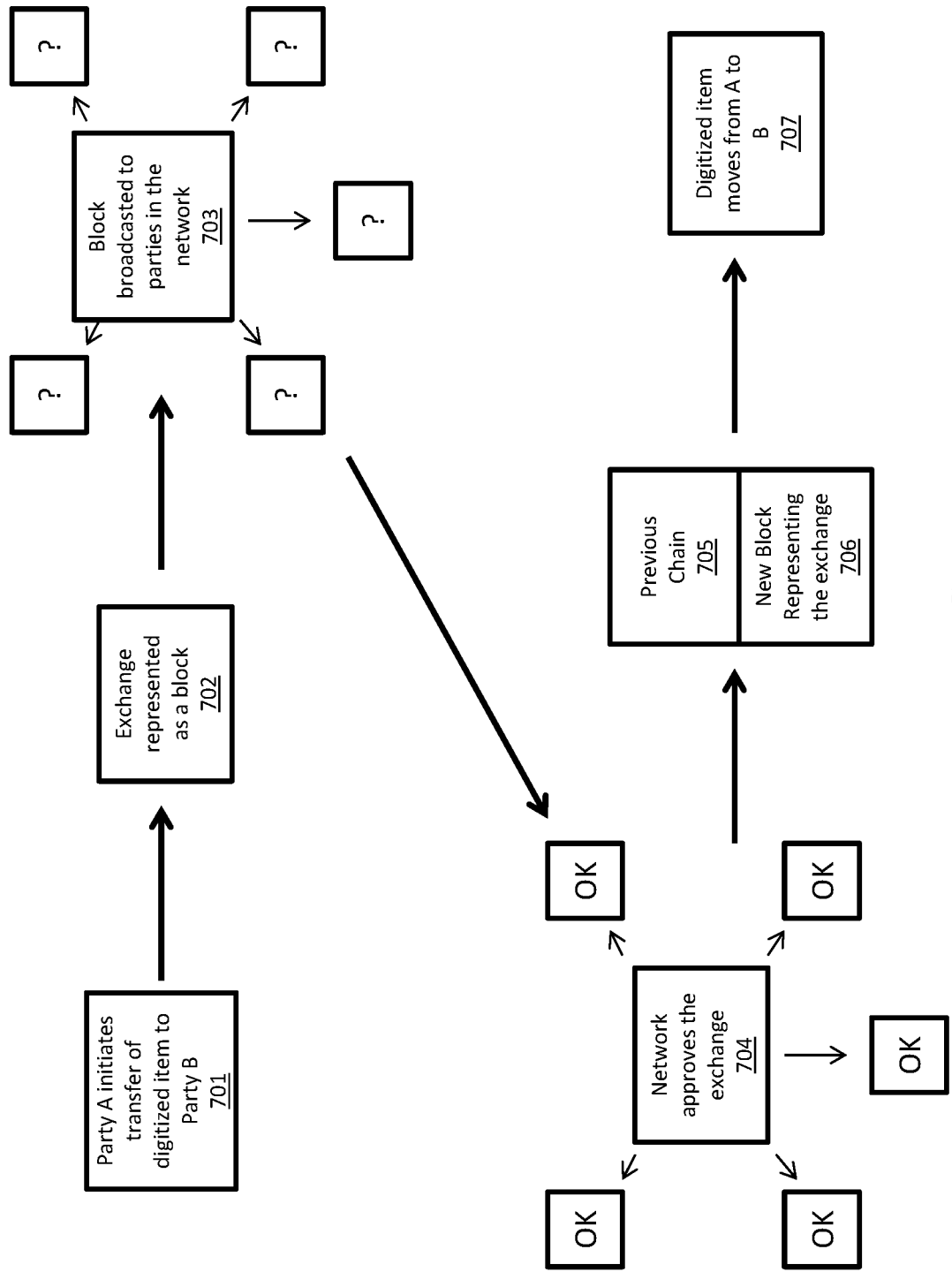
FIG. 7 comprises a process diagram as configured in accordance with various embodiments of these teachings.

Now referring to FIG. 7, a process diagram a blockchain update according to some implementations in shown. In step

701, party A initiates the transfer of a digitized item to party B. In some embodiments, the digitized item may comprise a digital currency, a digital asset, a document, rights to a physical asset, etc. In some embodiments, Party A may prove that he has possession of the digitized item by signing the transaction with a private key that may be verified with a public key in the previous transaction of the digitized item. In step 702, the exchange initiated in step 701 is represented as a block. In some embodiments, the transaction may be compared with transaction records in the longest chain in the distributed system to verify part A's ownership. In some embodiments, a plurality of nodes in the network may compete to form the block containing the transaction record. In some embodiments, nodes may be required to satisfy proof-of-work by solving a difficult mathematical problem to form the block. In some embodiments, other methods of proof such as proof-of-stake, proof-of-space, etc. may be used in the system. In some embodiments, the node that is first to form the block may earn a reward for the task as incentive. For example, in the Bitcoin system, the first node to provide prove of work to for block the may earn a Bitcoin. In some embodiments, a block may comprise one or more transactions between different parties that are broadcasted to the nodes. In step 703, the block is broadcasted to parties in the network. In step 704, nodes in the network approve the exchange by examining the block that contains the exchange. In some embodiments, the nodes may check the solution provided as proof-of-work to approve the block. In some embodiments, the nodes may check the transaction against the transaction record in the longest blockchain in the system to verify that the transaction is valid (e.g. party A is in possession of the asset he/she s seeks to transfer). In some embodiments, a block may be approved with consensus of the nodes in the network. After a block is approved, the new block 706 representing the exchange is added to the existing chain 705 comprising blocks that chronologically precede the new block 706. The new block 706 may contain the transaction(s) and a hash of one or more blocks in the existing chain 705. In some embodiments, each node may then update their copy of the blockchain with the new block and continue to work on extending the chain with additional transactions. In step 707, when the chain is updated with the new block, the digitized item is moved from party A to party B.

Figure 8:
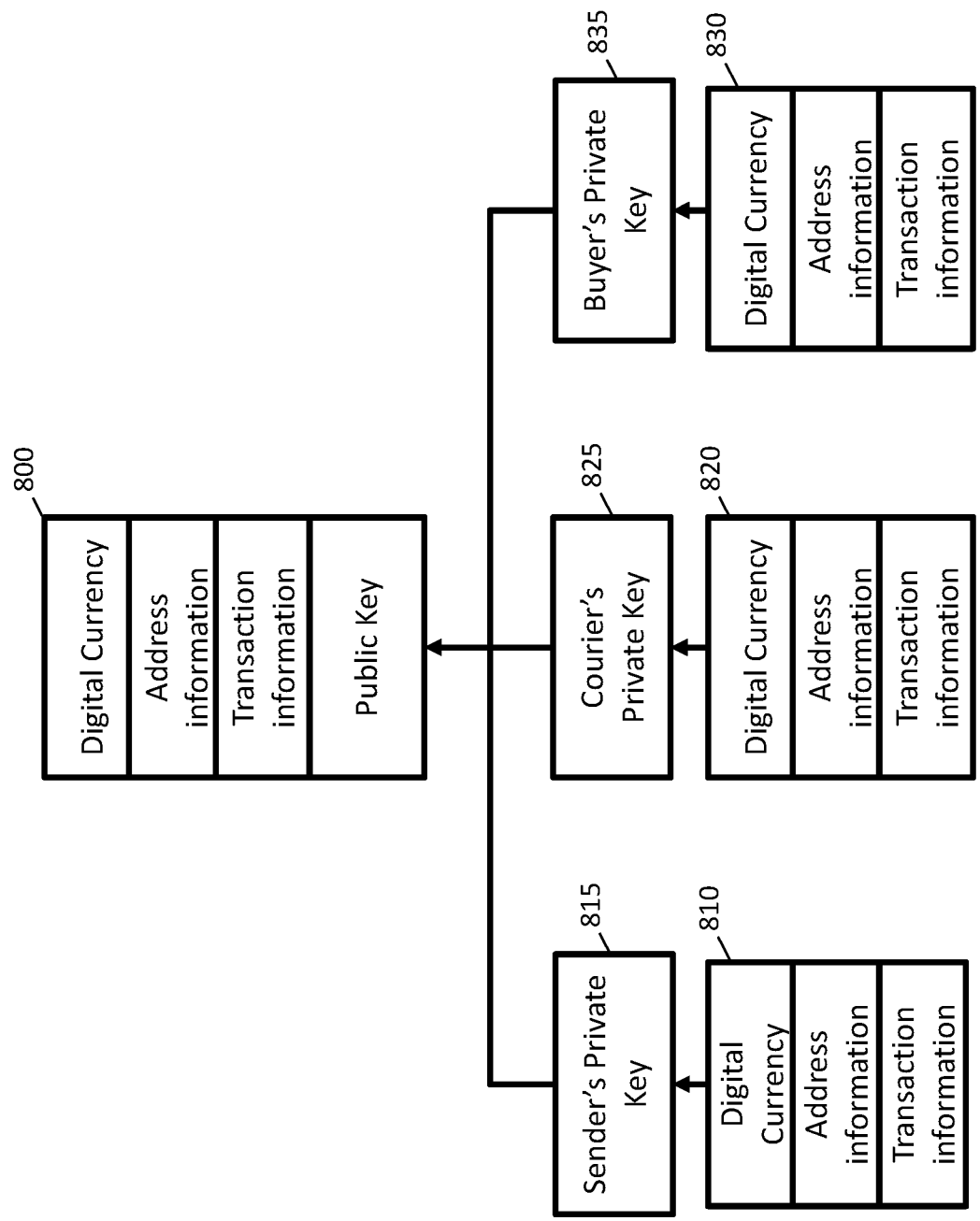
FIG. 8 comprises an illustration of a delivery record configured in accordance with various embodiments of these teachings.

Now referring to FIG. 8, a diagram of a blockchain according to some embodiments in shown. FIG. 8 comprises an example of an implementation of a blockchain system for delivery service record keeping. The delivery record 800 comprises digital currency information, address information, transaction information, and a public key associated with one or more of a sender, a courier, and a buyer. In some embodiments, nodes associated the sender, the courier, and the buyer may each store a copy of the delivery record 810, 820, and 830 respectively. In some embodiments, the delivery record 800 comprises a public key that allows the sender, the courier, and/or the buyer to view and/or update the delivery record 800 using their private keys 815, 825, and the 835 respectively. For example, when a package is transferred from a sender to the courier, the sender may use the sender's private key 815 to authorize the transfer of a digital asset representing the physical asset from the sender to the courier and update the delivery record with the new transaction. In some embodiments, the transfer from the seller to the courier may require signatures from both the sender and the courier using their respective private keys. The new transaction may be broadcasted and verified by the sender, the courier, the buyer, and/or other nodes on the system before being added to the distributed delivery record blockchain. When the package is transferred from the courier to the buyer, the courier may use the courier's private key 825 to authorize the transfer of the digital asset representing the physical asset from the courier to the buyer and update the delivery record with the new transaction. In some embodiments, the transfer from the courier to the buyer may require signatures from both the courier and the buyer using their respective private keys. The new transaction may be broadcasted and verified by the sender, the courier, the buyer, and/or other nodes on the system before being added to the distributed delivery record blockchain.

With the scheme shown in FIG. 8, the delivery record may be updated by one or more of the sender, courier, and the buyer to form a record of the transaction without a trusted third party while preventing unauthorized modifications to the record. In some embodiments, the blockchain-based transactions may further function to include transfers of digital currency with the completion of the transfer of physical asset. With the distributed database and peer-to-peer verification of a blockchain system, the sender, the courier, and the buyer can each have confidence in the authenticity and accuracy of the delivery record stored in the form of a blockchain.

Figure 9:
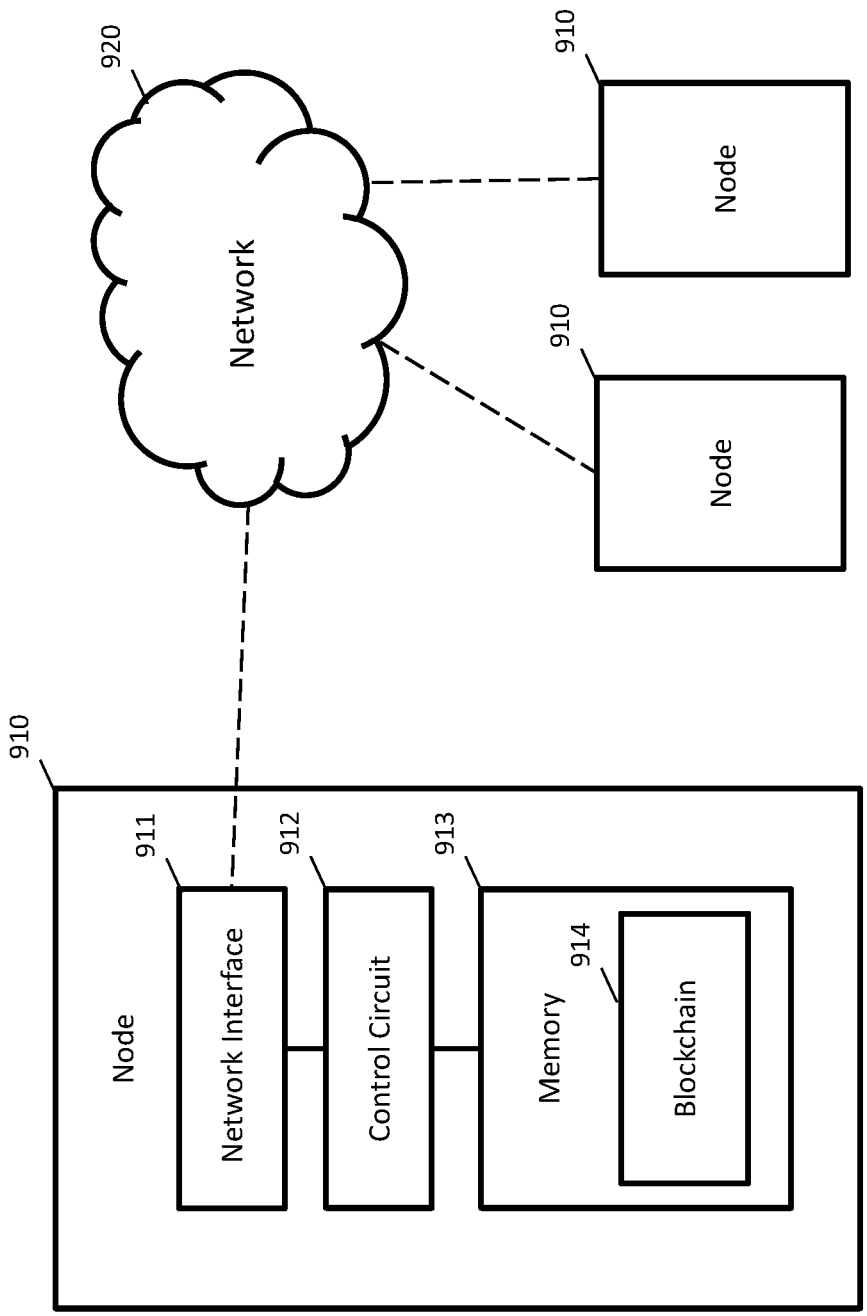
FIG. 9 comprise a system diagram configured in accordance with various embodiments of these teachings.

Now referring to FIG. 9, a system according to some embodiments is shown. A distributed blockchain system comprises a plurality of nodes 910 communicating over a network 920. In some embodiments, the nodes 910 may be comprise a distributed blockchain server and/or a distributed timestamp server. In some embodiments, one or more nodes 910 may comprise or be similar to a "miner" device on the Bitcoin network. Each node 910 in the system comprises a network interface 911, a control circuit 912, and a memory 913.

The control circuit 912 may comprise a processor, a microprocessor, and the like and may be configured to execute computer-readable instructions stored on a computer-readable storage memory 913. The computer-readable storage memory may comprise volatile and/or non-volatile memory and have stored upon it a set of computer-readable instructions which, when executed by the control circuit 912, causes the node 910 update the blockchain 914 stored in the memory 913 based on communications with other nodes 910 over the network 920. In some embodiments, the control circuit 912 may further be configured to extend the blockchain 914 by processing updates to form new blocks for the blockchain 914. Generally, each node may store a version of the blockchain 914, and together, may form a distributed database. In some embodiments, each node 910 may be configured to perform one or more steps described with reference to FIGS. 6-7 herein.

The network interface 911 may comprise one or more network devices configured to allow the control circuit to receive and transmit information via the network 920. In some embodiments, the network interface 911 may comprise one or more of a network adapter, a modem, a router, a data port, a transceiver, and the like. The network 920 may comprise a communication network configured to allow one or more nodes 910 to exchange data. In some embodiments, the network 920 may comprise one or more of the Internet, a local area network, a private network, a virtual private network, a home network, a wired network, a wireless network, and the like. In some embodiments, the system does not include a central server and/or a trusted third party system. Each node in the system may enter and leave the network at any time.

With the system and processes shown in, once a block is formed, the block cannot be changed without redoing the work to satisfy census rules thereby securing the block from tampering. A malicious attacker would need to provide proof standard for each block subsequent to the one he/she seeks to modify, race all other nodes, and overtake the majority of the system to affect change to an earlier record in the blockchain.

In some embodiments, blockchain may be used to support a payment system based on cryptographic proof instead of trust, allowing any two willing parties to transact directly with each other without the need for a trusted third party. Bitcoin is an example of a blockchain backed currency. A blockchain system uses a peer-to-peer distributed timestamp server to generate computational proof of the chronological order of transactions. Generally, a blockchain system is secure as long as honest nodes collectively control more processing power than any cooperating group of attacker nodes. With a blockchain, the transaction records are computationally impractical to reverse. As such, sellers are protected from fraud and buyers are protected by the routine escrow mechanism.

In some embodiments, a blockchain may use to secure digital documents such as digital cash, intellectual property, private financial data, chain of title to one or more rights, real property, digital wallet, digital representation of rights including, for example, a license to intellectual property, digital representation of a contractual relationship, medical records, security clearance rights, background check information, passwords, access control information for physical and/or virtual space, and combinations of one of more of the foregoing that allows online interactions directly between two parties without going through an intermediary. With a blockchain, a trusted third party is not required to prevent fraud. In some embodiments, a blockchain may include peer-to-peer network timestamped records of actions such as accessing documents, changing documents, copying documents, saving documents, moving documents, or other activities through which the digital content is used for its content, as an item for trade, or as an item for remuneration by hashing them into an ongoing chain of hash-based proof-of-work to form a record that cannot be changed in accord with that timestamp without redoing the proof-of-work.

In some embodiments, in the peer-to-peer network, the longest chain proves the sequence of events witnessed, proves that it came from the largest pool of processing power, and that the integrity of the document has been maintained. In some embodiments, the network for supporting blockchain-based record keeping requires minimal structure. In some embodiments, messages for updating the record are broadcast on a best-effort basis. Nodes can leave and rejoin the network at will and may be configured to accept the longest proof-of-work chain as proof of what happened while they were away.

In some embodiments, a blockchain-based system allows content use, content exchange, and the use of content for remuneration based on cryptographic proof instead of trust, allowing any two willing parties to employ the content without the need to trust each other and without the need for a trusted third party. In some embodiments, a blockchain may be used to ensure that a digital document was not altered after a given timestamp, that alterations made can be followed to a traceable point of origin, that only people with authorized keys can access the document, that the document itself is the original and cannot be duplicated, that where duplication is allowed and the integrity of the copy is maintained along with the original, that the document creator was authorized to create the document, and/or that the document holder was authorized to transfer, alter, or otherwise act on the document.

As used herein, in some embodiments, the term blockchain may refer to one or more of a hash chain, a hash tree, a distributed database, and a distributed ledger. In some embodiments, blockchain may further refer to systems that uses one or more of cryptography, private/public key encryption, proof standard, distributed timestamp server, and inventive schemes to regulate how new blocks may be added to the chain. In some embodiments, blockchain may refer to the technology that underlies the Bitcoin system, a "sidechain" that uses the Bitcoin system for authentication and/or verification, or an alternative blockchain ("altchain") that is based on bitcoin concept and/or code but are generally independent of the Bitcoin system.

Descriptions of embodiments of blockchain technology are provided herein as illustrations and examples only. The concepts of the blockchain system may be variously modified and adapted for different applications.

Those skilled in the art will recognize that a wide variety of other modifications, alterations, and combinations can also be made with respect to the above described embodiments without departing from the scope of the invention, and that such modifications, alterations, and combinations are to be viewed as being within the ambit of the inventive concept.

What is claimed is:

1. A system for automatically ordering a product item associated with sensed data from at least one sensor of a wearable portable user device comprising:
    at least one first sensor configured to provide first sensed data of a user of a wearable portable user device;
    at least one smart-device interface configured to receive at least one of: signaling data, default sensing exception data, and second sensed data associated with at least one smart device;
    at least one control circuit coupled to the at least one sensor and the at least one smart-device interface, the at least one control circuit configured to:
        determine whether the signaling data is received from the at least one smart-device interface at a first time;
        communicatively couple with the at least one smart device via the at least one smart-device interface in response to the determination that the signaling data is received;
        in response to communicatively coupling with the at least one smart device, prompt the user to select whether a first local database of the wearable portable user device or a second local database of the at least one smart device stores the first sensed data from the at least one first sensor and the second sensed data associated with the at least one smart device;
        in response to the user selecting the second local database of the at least one smart device, determine whether a previously stored data has been stored in the second local database for a time period at least equal to a threshold value;
        in response to the determination that the previously stored data has been stored in the second local database for the time period at least equal to the threshold value, delete the previously stored data from the second local database;
        copy a plurality of urgency threshold values from a remote database coupled to the at least one control circuit to the second local database, wherein the plurality of urgency threshold values is based on one or more inputs through a user interface operatively coupled to the at least one control circuit;
access the first sensed data from the second local database;
access the second sensed data from the second local database;
determine a product item associated with at least one of: the first sensed data and the second sensed data;
determine whether the at least one of: the first sensed data and the second sensed data has reached an urgency threshold value of the plurality of urgency threshold values; and
automatically initiate ordering and delivery of the product item when the urgency threshold value has been reached, wherein a mode of the delivery of the product item is based on the urgency threshold value; and
the remote database coupled to the at least one control circuit, the remote database configured to store the plurality of urgency threshold values.

2. The system of claim 1, wherein the plurality of urgency threshold values comprise a first value indicating a severe urgency instructing an automatic dispatch signal of an emergency medical service personnel to a location associated with the user, a second value indicating a high urgency instructing immediate delivery that is less than one day to the location, a third value indicating a medium urgency instructing at least one day or at least two days of delivery to the location, and a fourth value indicating a low urgency instructing no action.

3. The system of claim 1, wherein the at least one control circuit is further configured to:
determine whether the at least one of: the first sensed data and the second sensed data has reached a second urgency threshold value of the plurality of urgency threshold values; and
provide an automatic dispatch signal to an emergency medical service personnel when the second urgency threshold has been reached.

4. The system of claim 1, wherein the at least one control circuit is further configured to:
determine whether the at least one of: the first sensed data and the second sensed data has reached a second urgency threshold value of the plurality of urgency threshold values; and
determine no action when the second urgency threshold value has been reached.

5. The system of claim 1, wherein the at least one control circuit is further configured to:
determine whether the user of the wearable portable user device is at a retail store or en route to the retail store; and
in response to the determination that the user is at the retail store or en route to the retail store, add the product item to a shopping list associated with the user when the urgency threshold value has been reached instead of the automatic initiation of ordering and delivery of the product item.

6. The system of claim 1, further comprising the user interface operatively coupled to the at least one control circuit, the user interface configured to:
receive a first input of the one or more inputs from the user, wherein the first input corresponds to a goal that the user associates with the receipt of the at least one of: the first sensed data and the second sensed data by the at least one control circuit; and
receive a second input of the one or more inputs from the user, wherein the second input is associated with the goal and values associated with the plurality of urgency threshold values.

7. The system of claim 1, wherein the mode of the delivery of the product item is further based on cost of the delivery and distance to a delivery location, and wherein the determination of the product item is at least based on the one or more inputs.

8. The system of claim 1, wherein the at least one control circuit is further configured to:
determine whether the at least one of: the first sensed data and the second sensed data is associated with an automated variable dosing prescription defined by a doctor of the user, wherein the automated variable dosing prescription is a function of a doctor prescribed dosing limits particular to the user, and wherein the automatic initiation of ordering and delivery of the product item is further based on the determination that the at least one of: the first sensed data and the second sensed data is associated with the automated variable dosing prescription, the determination that the at least one of: the first sensed data and the second sensed data has reached the urgency threshold value, and a determination that the at least one of: the first sensed data and the second sensed data is less than a second urgency threshold value of the plurality of urgency threshold values; and
in response to the determination that the at least one of: the first sensed data and the second sensed data is associated with the automated variable dosing prescription and the determination that the at least one of: the first sensed data and the second sensed data has reached the urgency threshold value but less than the second urgency threshold value, modify an initial dosage prescribed by the doctor to the user based on the automated variable dosing prescription and the at least one of: the first sensed data and the second sensed data.

9. The system of claim 8 wherein, in the automatic initiation of ordering and delivery of the product item, the at least one control circuit is further configured to:
provide the modified initial dosage to a pharmacy associate;
order the product item, wherein the product item corresponds to a refill of a prescription associated with the user based on the modified initial dosage; and
notify the user via a user interface coupled to the wearable portable user device when the refill is complete, and the product item is ready for automatic delivery to a destination location associated with the user.

10. The system of claim 8, wherein the at least one control circuit is further configured to, in response to the determination that the at least one of: the first sensed data and the second sensed data is associated with the automated variable dosing prescription but prior to the determination that the at least one of: the first sensed data and the second sensed data has reached the urgency threshold value but less than the second urgency threshold value, determine whether the at least one of: the first sensed data and the second sensed data is at least a threshold from an average sensed data determined from historical sensed data received by the at least one control circuit over a time period; wherein the automatic initiation of ordering and delivery of the product item is further based on the determination that the at least one of:

the first sensed data and the second sensed data is at least the threshold from the average sensed data.

11. The system of claim 8, wherein the at least one control circuit is further configured to:
in response to the determination that the at least one of: the first sensed data and the second sensed data is associated with the automated variable dosing prescription but prior to the determination that the at least one of: the first sensed data and the second sensed data has reached the urgency threshold value but less than the second urgency threshold value, determine whether the at least one of: the first sensed data and the second sensed data is at least a threshold from an average sensed data determined from historical sensed data received by the at least one control circuit over a time period; and
cancel the automatic initiation of ordering and delivery of the product item based on the determination that the at least one of: the first sensed data and the second sensed data is at least the threshold from the average sensed data.

12. The system of claim 1, wherein the at least one control circuit is further configured to:
determine whether the signaling data is received from the at least one smart-device interface at a second time;
receive the default sensing exception data when the at least one smart device determines that an abnormal event affecting the user occurred;
in response to the receipt of the default sensing exception data, initiate receipts of the second sensed data and the first sensed data at the second time;
automatically initiate one or more predetermined action responses based on the second sensed data and the first sensed data received at the second time; and
initiate storage of the second sensed data and the first sensed data to the remote database.

13. A method for automatically ordering a product item associated with sensed data of a wearable portable user device comprising:
determining, by at least one control circuit of a wearable portable user device, whether signaling data is received from at least one smart-device interface of the wearable portable user device at a first time, wherein the at least one smart-device interface is configured to receive at least one of: the signaling data, default sensing exception data, and second sensed data associated with at least one smart device;
communicatively coupling the at least one control circuit with the at least one smart device in response to the determining that the signaling data is received;
in response to communicatively coupling the at least one control circuit with the at least one smart device, prompting a user of the wearable portable user device to select whether a first local database of the wearable portable user device or a second local database of the at least one smart device stores a first sensed data from at least one first sensor of the wearable portable user device and the second sensed data associated with the at least one smart device;
in response to the user selecting the second local database of the at least one smart device, determining whether a previously stored data has been stored in the second local database for a time period at least equal to a threshold value;
in response to determining that the previously stored data has been stored in the second local database for the time period at least equal to the threshold value, deleting the previously stored data from the second local database;
copying a plurality of urgency threshold values from a remote database coupled to the at least one control circuit to the second local database, wherein the plurality of urgency threshold values is based on one or more inputs through a user interface operatively coupled to the at least one control circuit;
accessing, by the at least one control circuit, the first sensed data;
accessing, by the at least one control circuit, the second sensed data;
determining, by the at least one control circuit, a product item associated with at least one of: the first sensed data and the second sensed data;
determining, by the at least one control circuit, whether the at least one of: the first sensed data and the second sensed data has reached an urgency threshold value of the plurality of urgency threshold values, wherein the plurality of urgency threshold values is stored in the remote database; and
automatically initiating an order and delivery of the product item when the urgency threshold value has been reached, wherein a mode of the delivery of the item is based on the urgency threshold value.

14. The method of claim 13, wherein the plurality of urgency threshold values comprise a first value indicating a severe urgency instructing an automatic dispatch signal of an emergency medical service personnel to a location associated with the user, a second value indicating a high urgency instructing immediate delivery that is less than one day to the location, a third value indicating a medium urgency instructing at least one day or at least two days of delivery to the location, and a fourth value indicating a low urgency instructing no action.

15. The method of claim 13, further comprising:
determining whether the at least one of: the first sensed data and the second sensed data has reached a second urgency threshold value of the plurality of urgency threshold values; and
providing an automatic dispatch signal to an emergency medical service personnel when the second urgency threshold has been reached.

16. The method of claim 13, further comprising:
determining whether the at least one of: the first sensed data and the second sensed data has reached a second urgency threshold value of the plurality of urgency threshold values; and
determining no action when the second urgency threshold value has been reached.

17. The method of claim 13, further comprising:
determining whether the user of the wearable portable user device is at a retail store or en route to the retail store; and
in response to the determining that the user is at the retail store or en route to the retail store, adding the product item to a shopping list associated with the user when the urgency threshold value has been reached instead of the automatically initiating the order and delivery of the product item.

18. The method of claim 13, wherein the mode of the delivery of the product item is further based on cost of the delivery and distance to a delivery location, and wherein the determining of the product item is at least based on the one or more inputs.

19. The method of claim 13, further comprising:
- determining whether the at least one of: the first sensed data and the second sensed data is associated with an automated variable dosing prescription defined by a doctor of the user, wherein the automated variable dosing prescription is a function of a doctor prescribed dosing limits particular to the user, and wherein the automatically initiating the order and delivery of the product item is further based on the determining that the at least one of: the first sensed data and the second sensed data is associated with the automated variable dosing prescription, the determining that the at least one of: the first sensed data and the second sensed data has reached the urgency threshold value, and determining that the at least one of: the first sensed data and the second sensed data is less than a second urgency threshold value of the plurality of urgency threshold values; and
- in response to the determining that the at least one of: the first sensed data and the second sensed data is associated with the automated variable dosing prescription and the determining that the at least one of: the first sensed data and the second sensed data has reached the urgency threshold value but less than the second urgency threshold value, modifying an initial dosage prescribed by the doctor to the user based on the at least one of: the first sensed data and the second sensed data and the automated variable dosing prescription.

20. The method of claim 19, wherein the automatically initiating the order and delivery of the product item further comprises:
- providing the modified initial dosage to a pharmacy associate;
- ordering the product item, wherein the product item corresponds to a refill of a prescription associated with the user based on the modified initial dosage; and
- notifying the user via a user interface coupled to the wearable portable user device when the refill is complete, and the product item is ready for an automatic delivery to a destination location associated with the user.

21. The method of claim 19, further comprising:
- in response to the determining that the at least one of: the first sensed data and the second sensed data is associated with the automated variable dosing prescription but prior to the determining that the at least one of: the first sensed data and the second sensed data has reached the urgency threshold value but less than the second urgency threshold value, determining whether the at least one of: the first sensed data and the second sensed data is at least a threshold from an average sensed data determined from historical sensed data received by the at least one control circuit over a time period; and
- cancelling the automatically initiating the order and delivery of the product item based on the determining that the at least one of: the first sensed data and the second sensed data is at least the threshold from the average sensed data.

22. The method of claim 21, further comprising:
- determining whether the signaling data is received from the at least one smart-device interface at a second time;
- receiving the default sensing exception data when the at least one smart device determines that an abnormal event affecting the user occurred;
- in response to the receiving of the default sensing exception data, initiating receipts of the second sensed data and the first sensed data at the second time;
- automatically initiating one or more predetermined action responses based on the second sensed data and the first sensed data received at the second time; and
- initiating storage of the second sensed data and the first sensed data to the remote database.

\* \* \* \* \*